(12) United States Patent
Blackshear

(10) Patent No.: US 8,309,313 B2
(45) Date of Patent: Nov. 13, 2012

(54) GLYCATED PEPTIDES AND METHODS OF USE

(75) Inventor: Perry J. Blackshear, Chapel Hill, NC (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 999 days.

(21) Appl. No.: 12/281,909

(22) PCT Filed: Mar. 6, 2007

(86) PCT No.: PCT/US2007/063385
§ 371 (c)(1),
(2), (4) Date: Oct. 27, 2008

(87) PCT Pub. No.: WO2007/117794
PCT Pub. Date: Oct. 18, 2007

(65) Prior Publication Data
US 2009/0093066 A1    Apr. 9, 2009

Related U.S. Application Data

(60) Provisional application No. 60/779,710, filed on Mar. 6, 2006.

(51) Int. Cl.
*G01N 33/53* (2006.01)
*G01N 31/00* (2006.01)

(52) U.S. Cl. ............ 435/7.21; 435/7.1; 436/1; 436/501; 436/518; 424/9.1; 424/520; 422/1; 422/50; 530/300; 530/350

(58) Field of Classification Search .................. None
See application file for complete search history.

(56) References Cited

FOREIGN PATENT DOCUMENTS

| EP | 1 142 996 A1 | 10/2001 |
| EP | 1 624 307 A2 | 2/2006 |
| WO | WO 2004/027430 A1 * | 4/2004 |
| WO | WO 2005/114190 A2 * | 12/2005 |

OTHER PUBLICATIONS

Yan et al. (Diabetes Technology & Therapeutics, vol. 4, No. 3, Nov. 3, 2002, pp. 339-345.*
Armbruster, *Clin. Chem.*, 33 (12), 2153-2163 (1987).
Bunn et al., *Prog. Clin. Biol. Res.*, 60, 83-94 (1981).
Bunn, *Schweiz Med. Wochenschr.*, 111 (41), 1503-1507 (1981).
De Vegt et al., *Diabetologia*, 42, 926-931 (1999).
Gabbay et al., *J. Clin. Endocrinol. Metab.*, 44, 859-864 (1977).
Gruber et al., *J. Pept. Res.*, 66, 111-124 (2005).
Heinrikson, *J. Biol. Chem.*, 241 (6), 1393-1405 (1966).
Jaleel et al., *Diabetes Care*, 28 (3), 645-652 (2005).
Kouzuma et al., *Clin. Chim. Acta*, 324, 61-71 (2002).
Nathan et al., *N. Engl. J. Med.*, 353, 2643-2653 (2005).
Nowatzke et al., *Clin. Chim. Acta*, 350, 201-209 (2004).
Rohlfing et al., *Diabetes Care*, 23 (2), 187-191 (2000).
Shapiro et al., *Metabolism*, 28 (4), Supp. 1, 427-430 (1979).
Steffes, *Clin. Chem.*, 41 (2), 180-181 (1995).
UK Prospective Diabetes Study Group, *Lancet*, 352, 837-853 (1998).

* cited by examiner

*Primary Examiner* — Lisa Cook
(74) *Attorney, Agent, or Firm* — Leydig, Voit & Mayer, Ltd.

(57) ABSTRACT

The invention provides glycated peptides and glycated fragments and glycated variants thereof, antibodies and aptamers which bind thereto, compositions and kits comprising the same, related conjugates, and a database comprising data indicating the concentration of glycated peptides present in diabetic and non-diabetic persons. The invention also provides a method of monitoring glycemic control, a method of treating or preventing diabetes, a method of preventing a complication of diabetes, a method of monitoring the status of diabetes, a method of determining the efficacy of a diabetes treatment, as well as methods of detecting diabetes or a predisposition thereto.

14 Claims, No Drawings

GLYCATED PEPTIDES AND METHODS OF USE

CROSS-REFERENCE TO RELATED APPLICATIONS

This is a national phase patent application under 35 U.S.C. §371 of International Application No. PCT/US/2007/063385, which claims the benefit of U.S. Provisional Patent Application No. 60/779,710, filed Mar. 6, 2006, which are specifically incorporated by reference herein in their entirety.

SEQUENCE LISTING

Incorporated by reference in its entirety herein is a computer-readable nucleotide/amino acid sequence listing submitted concurrently herewith and identified as follows: One 110,954 byte ASCII (Text) file named "703368 ST25.txt," created on Sep. 5, 2008.

BACKGROUND OF THE INVENTION

Improved glycemic control can delay and possibly prevent the development of some of the long-term microvascular and, perhaps, macrovascular complications of both type 1 and type 2 diabetes (The Diabetes Control and Complications Trial Research Group, *N Engl J Med* 329: 977-986 (1993) and UK Prospective Diabetes Study Group, *Lancet* 352: 837-853 (1998); Nathan et al., *N Engl J Med* 353: 2643-2653 (2005)). Thus, improving day-to-day glycemic control in diabetes is one of the main goals of current therapy.

The current accepted method of monitoring glycemic control is by measuring the relative concentration of glycated red-cell hemoglobin, also known as hemoglobin A1C (HbA1C), wherein high levels of HbA1C typically indicate poor glycemic control. Glycation of hemoglobin involves the non-enzymatic covalent attachment of multiple glucose molecules to the amino terminal and internal lysine residues in the hemoglobin A molecule (Bunn, *Schweiz Med Wochenschr* 111: 1503-1507 (1981); Bunn et al., *Prog Clin Biol Res* 60: 83-94 (1981); Gabbay et al., *J Clin Endocrinol Metab* 44: 859-864 (1977); and Shapiro et al., *Metabolism* 28: 427-430 (1979)). Glycation results in electrophoretic and other changes in the behavior of the hemoglobin molecule such that its concentration as a fraction of the total hemoglobin can be readily measured.

It has been shown that the relative concentration of HbA1C as compared to total hemoglobin concentration reflects the glycemic control of a patient over a period of several months, presumably based on the lifetime of the erythrocyte in the circulation of approximately 120 days. However, measurement of HbA1C provides an imperfect index of glycemic control. Due to the relatively long period of time reflected in a single HbA1C measurement, acute modifications in glycemic control do not result in rapid changes in HbA1C levels. Also, HbA1C levels can be affected by artifacts caused by conditions such as thalassemia, uremia, and hypertriglyceridemia, as well as by drugs or other ingested substances, such as aspirin, penicillin, and ethanol.

Furthermore, HbA1C measurements are relatively insensitive to minor changes in glucose tolerance, which are now viewed as predictors of diabetes development (Rohlfing et al., *Diabetes Care* 23: 187-191 (2000)). Moreover, the incidence of cardiovascular disease appears to be linked to concentrations of HbA1C within the conventional "normal" range, even in the absence of known diabetes (de Vegt et al., *Diabetologia* 42: 926-931 (1999)).

Due to the limitations of the HbA1C assay, attempts have been made to develop new biomarkers of glycemic control. For instance, fructosamine, 1,5-anhydroglucitol (1,5AG), and albumin have been tested as a glycemic control markers (Armbruster, *Clin Chem* 33: 2153-2163 (1987); Nowatzke et al., *Clin Chim Acta* 350: 201-209 (2004); (Kouzuma et al., *Clin Chim Acta* 324: 61-71 (2002)). However, none of these biomarkers have gained widespread use.

Accordingly, there is a need for new methods and compositions that can be used to monitor glycemic control or detect abnormal glycemic control associated with the onset or progression of diabetes. The invention provides such methods and compositions.

BRIEF SUMMARY OF THE INVENTION

The invention provides an isolated or purified glycated peptide comprising (i) at least one of Peptides AA-DJ or (ii) an amino acid sequence selected from the group consisting of SEQ ID NOs: 24-36, or a glycated fragment or glycated variant thereof.

The invention also provides an isolated or purified antibody, an antigen binding portion thereof, or an aptamer, any of which specifically binds to the glycated peptide described herein, or a glycated fragment or glycated variant thereof.

The invention further provides a conjugate comprising (i) a glucose-binding moiety, (ii) an antibody, antigen binding portion thereof, or aptamer which specifically binds to a peptide, or a fragment or variant thereof, comprising (a) at least one of Peptides AA-DJ or (b) an amino acid sequence selected from the group consisting of SEQ ID NOs: 24-36, and (iii) a detectable label.

Compositions and kits comprising any of the glycated peptides, or a glycated fragment or glycated variant thereof, antibodies or antigen binding portions thereof, aptamers, or conjugates described herein are further provided by the invention.

Also provided is a database comprising data indicating the concentration of one or more of the glycated peptides described herein, or a glycated fragment or glycated variant thereof, present in diabetic persons, non-diabetic persons, or both diabetic and non-diabetic persons.

The invention further provides a method of monitoring glycemic control of a host. The method comprises measuring the concentration of a glycated peptide, or a glycated fragment or glycated variant thereof, in a host, wherein the glycated peptide comprises (i) at least one of Peptides AA-DJ or (ii) an amino acid sequence of the group consisting of SEQ ID NOs: 24-36.

Furthermore, the invention provides a method of treating or preventing diabetes or a complication of diabetes, a method of detecting the onset, progression, or regression of diabetes, a method of detecting diabetes or a predisposition to diabetes, and a method of determining the efficacy of a diabetes treatment. The methods comprise monitoring the glycemic control of a host in accordance with the invention, or other method steps described herein.

DETAILED DESCRIPTION OF THE INVENTION

The invention provides isolated or purified glycated peptides, as well as glycated fragments and glycated variants thereof. The glycated peptides comprise (i) at least one of Peptides AA-DJ or (ii) an amino acid sequence selected from the group consisting of SEQ ID NOs: 24-36.

Glycated Peptides AA-DJ were found to be significantly increased in concentration in diabetic patients as compared to non-diabetic patients, as discussed further herein. Peptides AA-DJ can be isolated upon carrying out the procedures described in Example 1. Specifically, all of Peptides AA-DJ are glycated tryptic peptides of plasma proteins that can be enriched in a plasma sample using affinity chromatography with m-aminophenylboronic acid. Such a procedure is explained in greater detail in Example 1. Further, Peptides AA-DJ have the specific properties set forth in Table 1, wherein m/z is the mass in Daltons per unit of charge (z) as determined by a mass spectrometer, R.T. (min) is the retention time on an HPLC column in minutes, z is the net charge of the peptide, and M+H is the calculated mass of the protonated peptide. The fold-change in the concentration of each of the peptides in diabetic patients as compared to diabetic patients also is provided in Table 1, as further discussed in the examples.

TABLE 1

| Peptide | m/z | R.T. (min.) | z | m + H | Amino Acid Sequence | SEQ ID NO | P-value | Fold-change* |
|---|---|---|---|---|---|---|---|---|
| AA | 440.24 | 38.11 | 3 | 1318.70 | SKEQLTPLIK | 1 | 7.54E-12 | 5.97 |
| AB | 529.27 | 37.78 | 3 | 1585.80 | | | 7.87E-11 | 7.77 |
| AC | 397.20 | 37.80 | 4 | 1585.78 | | | 2.47E-10 | 7.35 |
| AD | 482.93 | 31.70 | 3 | 1446.78 | | | 5.07E-10 | 6.73 |
| AE | 362.45 | 31.69 | 4 | 1446.78 | | | 1.00E-09 | 7.06 |
| AF | 400.22 | 41.66 | 3 | 1198.65 | | | 3.78E-09 | 8.20 |
| AG | 659.86 | 38.10 | 2 | 1318.72 | SKEQLTPLIK | 1 | 7.20E-09 | 7.46 |
| AH | 312.17 | 28.79 | 3 | 934.50 | | | 1.69E-08 | 7.99 |
| AI | 428.22 | 27.51 | 3 | 1282.63 | SIYKPGQTVK | 2 | 3.62E-08 | 8.36 |
| AJ | 318.17 | 28.79 | 3 | 952.50 | | | 5.22E-08 | 8.05 |
| AK | 342.52 | 31.49 | 3 | 1025.55 | | | 6.58E-08 | 8.73 |
| AL | 454.56 | 28.69 | 3 | 1361.66 | VKSPELQAEAK | 3 | 7.21E-08 | 6.18 |
| AM | 336.52 | 31.49 | 3 | 1007.54 | | | 9.94E-08 | 8.57 |
| AN | 476.76 | 28.78 | 2 | 952.52 | | | 1.89E-07 | 9.02 |
| AO | 599.84 | 41.65 | 2 | 1198.67 | | | 2.43E-07 | 9.51 |
| AP | 466.91 | 37.05 | 3 | 1398.72 | LVDGKGVPIPNK | 4 | 7.37E-07 | 8.16 |
| AQ | 366.85 | 24.00 | 3 | 1098.53 | | | 9.61E-07 | 8.99 |
| AR | 394.55 | 28.14 | 3 | 1181.64 | | | 1.69E-06 | 10.10 |
| AS | 544.93 | 38.65 | 3 | 1632.77 | SKAIGYLNTGYQR | 5 | 1.73E-06 | 9.61 |
| AT | 414.88 | 35.20 | 3 | 1242.61 | | | 2.74E-06 | 7.06 |
| AU | 374.93 | 46.61 | 4 | 1496.71 | | | 3.52E-06 | 12.42 |
| AV | 507.76 | 29.87 | 2 | 1014.51 | | | 4.08E-06 | 5.29 |
| AW | 433.21 | 28.41 | 3 | 1297.60 | QKLHELQEK | 6 | 4.12E-06 | 3.88 |
| AX | 412.96 | 35.46 | 4 | 1648.82 | | | 4.16E-06 | 8.14 |
| AY | 365.18 | 24.30 | 3 | 1093.52 | | | 4.39E-06 | 5.25 |
| AZ | 344.52 | 41.31 | 3 | 1031.56 | | | 9.79E-06 | 5.55 |
| BA | 440.88 | 27.49 | 3 | 1320.61 | | | 1.30E-05 | 5.51 |
| BB | 525.30 | 41.31 | 2 | 1049.58 | GKITDLIK | 7 | 1.34E-05 | 5.78 |
| BC | 392.20 | 33.7S | 3 | 1174.58 | | | 1.43E-05 | 5.43 |
| BD | 451.55 | 29.96 | 3 | 1352.63 | | | 1.83E-05 | 8.90 |
| BE | 649.32 | 28.40 | 2 | 1297.63 | QKLHELQEK | 6 | 1.97E-05 | 6.22 |
| BF | 580.29 | 30.80 | 2 | 1159.57 | | | 2.08E-05 | 5.42 |
| BG | 381.18 | 32.68 | 4 | 1521.70 | | | 2.43E-05 | 5.45 |

TABLE 1-continued

| Peptide | m/z | R.T. (min.) | z | m + H | Amino Acid Sequence | SEQ ID NO | P-value | Fold-change* |
|---|---|---|---|---|---|---|---|---|
| BH | 440.55 | 26.45 | 3 | 1319.63 | LEALKENGGAR | 8 | 2.61E-05 | 4.65 |
| BI | 499.73 | 26.68 | 2 | 998.45 | | | 2.64E-05 | 5.35 |
| BJ | 327.48 | 26.70 | 3 | 980.43 | | | 2.70E-05 | 4.78 |
| BK | 461.57 | 47.69 | 3 | 1382.70 | | | 3.02E-05 | 10.90 |
| BL | 350.53 | 41.28 | 3 | 1049.57 | GKITDLIK | 7 | 3.03E-05 | 5.66 |
| BM | 516.23 | 34.59 | 3 | 1546.68 | | | 3.28E-05 | 6.53 |
| BN | 514.91 | 41.89 | 3 | 1542.71 | VQPYLDDFQKK | 9 | 3.44E-05 | 5.41 |
| BO | 402.70 | 35.33 | 4 | 1607.76 | GDJVWVYPPEKK | 10 | 3.48E-05 | 6.20 |
| BP | 336.50 | 28.74 | 3 | 1007.47 | | | 3.49E-05 | 6.08 |
| BQ | 581.29 | 40.20 | 3 | 1741.85 | | | 3.73E-05 | 5.87 |
| BR | 335.85 | 22.85 | 3 | 1005.54 | | | 3.95E-05 | 6.00 |
| BS | 309.18 | 27.36 | 3 | 925.51 | | | 4.02E-05 | 2.24 |
| BT | 399.51 | 25.34 | 3 | 1196.53 | | | 4.04E-05 | 6.66 |
| BU | 481.98 | 35.08 | 4 | 1924.88 | VKAHYGGFTVQNEANK | 11 | 4.25E-05 | 7.15 |
| BV | 403.21 | 31.31 | 3 | 1207.63 | | | 4.52E-05 | 6.22 |
| BW | 587.81 | 33.74 | 2 | 1174.61 | | | 4.59E-05 | 6.39 |
| BX | 436.21 | 40.21 | 4 | 1741.83 | | | 4.66E-05 | 5.88 |
| BY | 536.60 | 35.34 | 3 | 1607.78 | GDJVVVVYPPEKK | 10 | 4.81E-05 | 6.10 |
| BZ | 493.90 | 40.03 | 3 | 1479.68 | GDJVWVYPPEK | 12 | 5.42E-05 | 6.21 |
| CA | 333.48 | 26.69 | 3 | 998.43 | | | 5.65E-05 | 4.80 |
| CB | 507.59 | 39.15 | 3 | 1520.75 | | | 5.74E-05 | 9.28 |
| CC | 467.26 | 40.46 | 4 | 1866.03 | | | 7.48E-05 | 12.89 |
| CD | 374.20 | 27.40 | 3 | 1120.60 | | | 7.76E-05 | 3.21 |
| CE | 642.30 | 35.08 | 3 | 1924.90 | VKAHYGGFTVQNEANK | 11 | 8.40E-05 | 7.47 |
| CF | 350.82 | 20.59 | 3 | 1050.45 | SYFEKSK | 13 | 1.00E-04 | 4.73 |
| CG | 436.55 | 36.19 | 3 | 1307.64 | VVVVYPPEKK | 14 | 1.01E-04 | 6.35 |
| CH | 427.21 | 28.43 | 3 | 1279.61 | | | 1.02E-04 | 5.34 |
| CI | 477.90 | 40.65 | 3 | 1431.69 | | | 1.14E-04 | 6.81 |
| CJ | 374.86 | 22.34 | 3 | 1122.56 | | | 1.62E-04 | 5.49 |
| CK | 575.27 | 21.39 | 3 | 1723.78 | AGVETTTPSKQSNNK | 15 | 1.93E-04 | 5.42 |
| CL | 410.22 | 36.53 | 4 | 1637.86 | | | 2.07E-04 | 7.69 |
| CM | 374.85 | 29.12 | 3 | 1122.54 | | | 2.48E-04 | 9.25 |
| CN | 548.26 | 37.01 | 4 | 2190.00 | | | 3.28E-04 | 6.79 |
| CO | 349.20 | 32.63 | 3 | 1045.58 | | | 3.42E-04 | 9.62 |
| CP | 438.89 | 20.05 | 3 | 1314.64 | | | 5.38E-04 | 5.75 |
| CQ | 467.58 | 36.49 | 3 | 1400.72 | | | 7.42E-04 | 6.53 |
| CR | 637.54 | 50.20 | 4 | 2547.14 | | | 8.39E-04 | 15.86 |
| CS | 386.22 | 38.35 | 3 | 1156.65 | | | 8.63E-04 | 2.70 |

TABLE 1-continued

| Peptide | m/z | R.T. (min.) | z | m + H | Amino Acid Sequence | SEQ ID NO | P-value | Fold-change* |
|---|---|---|---|---|---|---|---|---|
| CT | 434.54 | 38.50 | 3 | 1301.61 | | | 1.30E-03 | 1.63 |
| CU | 427.22 | 46.06 | 3 | 1279.66 | GFSPKDVLVR | 16 | 1.45E-03 | 7.26 |
| CV | 402.23 | 51.18 | 3 | 1204.68 | LKFIIPSPK | 17 | 1.89E-03 | 4.95 |
| CW | 347.50 | 21.62 | 3 | 1040.47 | | | 2.07E-03 | 2.50 |
| CX | 430.19 | 40.37 | 3 | 1288.57 | KASYLDCIR | 18 | 3.10E-03 | 5.60 |
| CY | 379.20 | 28.27 | 3 | 1135.57 | | | 3.95E-03 | 4.32 |
| CZ | 511.99 | 33.71 | 4 | 2044.94 | GDVAFVKHQTVPQNTGGK | 19 | 3.99E-03 | 4.16 |
| DA | 466.27 | 37.30 | 1 | 466.27 | | | 4.23E-03 | 1.96 |
| DB | 476.92 | 33.84 | 3 | 1428.74 | VSNKALPAPIEK | 20 | 5.58E-03 | 6.34 |
| DC | 383.54 | 30.74 | 3 | 1148.60 | KQLVEIEK | 21 | 7.53E-03 | 5.83 |
| DD | 443.85 | 27.02 | 3 | 1329.52 | | | 7.55E-03 | 3.99 |
| DE | 443.72 | 31.80 | 2 | 886.43 | | | 1.03E-02 | 1.69 |
| DF | 538.59 | 44.23 | 3 | 1613.75 | AKVQPYLDDFQK | 22 | 1.23E-02 | 5.47 |
| DG | 337.16 | 24.45 | 2 | 673.30 | | | 1.30E-02 | 1.48 |
| DH | 461.52 | 27.70 | 3 | 1382.55 | | | 2.80E-02 | -2.45 |
| DI | 403.23 | 42.18 | 2 | 805.46 | | | 3.65E-02 | 1.44 |
| DJ | 538.26 | 45.44 | 3 | 1612.77 | | | 4.59E-02 | 4.13 |

*Fold-increase in diabetic vs. non-diabetic patients is indicated by a positive number, and fold-decreases are indicated by a negative number Without wishing to be bound by any particular theory, it is believed that some of Peptides AA-DJ are glycated fragments of a protein comprising an amino acid sequence selected from the group consisting of SEQ ID NOs: 24-36. For instance, it is contemplated that Peptide AA is a glycated fragment of SEQ ID NO: 24 (the amino acid sequence of Apolipoprotein A-II protein), Peptide AI is a glycated fragment of the SEQ ID NO: 25 (the amino acid sequence of α-2 macroglobulin protein), and Peptide BL is a glycated fragment of SEQ ID NO: 27 (the amino acid sequence of α-1 antichymotrypsin protein). Other such associations are set forth in Table 2. In this regard, the glycated peptide of the invention can comprise an amino acid sequence selected from the group consisting of SEQ ID NOs: 24-36, which correspond to the mature proteins identified in Table 2.

The invention also provides glycated fragments of the glycated peptides described herein. The term "glycated fragment" when used in reference to a glycated peptide refers to any contiguous portion of 2, 3, 4, 5 or more amino acid residues of the glycated peptide of the invention, which portion comprises at least one of the glycated amino acid residues of the glycated peptide from which it originates (e.g., the "parent" glycated peptide) and a sufficient number of amino acid residues of the parent glycated peptide that flank the at least one glycated amino acid residue such that the glycated fragment can be detected for purposes of measuring its concentration. The concentration of the glycated fragment reflects the concentration of the parent glycated peptide. In reference to the parent glycated peptide, the glycated fragment can comprise, for instance, about 10%, 25%, 30%, 50%, 68%, 80%, 90%, 95%, or more contiguous amino acids of the parent peptide. In a preferred embodiment, the glycated fragment comprises 5 or more amino acids, such that a binding molecule or other agent used to detect the fragment, e.g., an antibody, aptamer, or conjugate comprising a glucose binding moiety, can bind to the glycated fragment.

The glycated fragment can comprise additional amino acids at the amino or carboxy terminus of the fragment, or at both termini, which additional amino acids are not found in the amino acid sequence of the parent glycated peptide. Desirably, the additional amino acids do not interfere with the ability of the glycated fragment to be detected.

Non-limiting examples of glycated fragments of peptides comprising SEQ ID NOs: 24-36 include, for example, peptides comprising an amino acid sequence selected from the group consisting of SEQ ID NOs: 1-23.

TABLE 2

| Peptide | Protein Description | Accession No.[1] | SEQ ID NO: |
|---|---|---|---|
| AA | Apolipoprotein A-II (Apo-AII) | NP_001634.1 | 24 |
| AG | Apolipoprotein A-II (Apo-AII) | NP_001634.1 | 24 |
| AI | Alpha-2-macroglobulin (Alpha-2-M) | NP_000005.2 | 25 |
| AL | Apolipoprotein A-II (Apo-AII) | NP_001634.1 | 24 |
| AP | Alpha-2 macroglobulin (Alpha 2M) | NP_000005.2 | 25 |
| AS | Alpha-2 macroglobulin (Alpha 2M) | NP_000005.2 | 25 |
| AW | Apolipoprotein A-I (Apo-AI) | NP_000030.1 | 26 |
| BB | Alpha-1-antichymotrypsin (ACT) | NP_001076.2 | 27 |
| BE | Apolipoprotein A-I (Apo-AI) | NP_000030.1 | 26 |
| BH | Apolipoprotein A-I (Apo-AI) | NP_000030.1 | 26 |
| BL | Alpha-1-antichymotrypsin (ACT) | NP_001076.2 | 27 |
| BN | Apolipoprotein A-I (Apo-AI) | NP_000030.1 | 26 |
| BO | Hemopexin (Beta-1B-glycoprotein) | NP_000604.1 | 28 |
| BU | Fibrinogen, beta chain | NP_005132.2 | 29 |
| BY | Hemopexin (Beta-1B-glycoprotein) | NP_000604.1 | 28 |

TABLE 2-continued

| Peptide | Protein Description | Accession No.[1] | SEQ ID NO: |
|---|---|---|---|
| BZ | Hemopexin (Beta-1B-glycoprotein) | NP_000604.1 | 28 |
| CE | Fibrinogen, beta chain | NP_005132.2 | 29 |
| CF | Apolipoprotein A-II (Apo-AII) | NP_001634.1 | 24 |
| CG | Hemopexin (Beta-1B-glycoprotein) | NP_000604.1 | 28 |
| CK | Ig lambda light chain | AAA59109 | 30 |
| CU | Ig heavy chain, constant region | CAA09968 | 31 |
| CV | Apolipoprotein B-100 (Apo B-100) | NP_000375.1 | 32 |
| CV | Apolipoprotein B-48 (Apo B-48) | NP_000375.1 | 33 |
| CX | Transferrin | NP_001054.1 | 34 |
| CZ | Transferrin | NP_001054.1 | 34 |
| DB | IhHG1 | AAH19046 | 35 |
| DC | Haptoglobin | NP_005134.1 | 36 |
| DF | Apolipoprotein A-I (Apo-AI) | NP_000030.1 | 26 |

[1]Accession number of the GenBank database of the National Center for Biotechnology Information. In some instances, the accession number corresponds directly to a precursor protein sequence, with reference to the sequence of the mature protein. The precursor protein sequences, where applicable, are hereby incorporated by reference to the accession number.

The invention also provides glycated variants of the glycated peptides described herein. The term "glycated variant" when used in reference to a glycated peptide refers to a to a glycated peptide having substantial or significant sequence identity or similarity to a "parent" glycated peptide otherwise described herein (e.g., Peptides AA-DJ). The glycated variant preferably retains any activity that the parent glycated peptide may have. Glycated variants encompass, for example, those variants of a glycated peptide described herein (i.e., the parent glycated peptide) that retain the at least one glycated amino acid residue of the parent glycated peptide and retain sufficient sequence identity of the parent glycated peptide, such that the glycated variant can be detected for the purposes of measuring its concentration. In reference to the parent glycated peptide, the glycated variant can, for instance, have a sequence identity to the parent glycated peptide (e.g., comprising glycated Peptides AA-DJ or SEQ ID NOs: 24-36) of 30%, 50%, 75%, 80%, 90%, 95%, 98% or more. Sequence identity can be determined, for instance, using the Basic Local Alignment Search Tool (BLAST), made publicly available through the National Center for Biotechnology Information (NCBI), Bethesda, Md.

The glycated variant can, for example, comprise a variation of the amino acid sequence of the parent glycated peptide, or a glycated fragment thereof, wherein one or more amino acid residues of the parent amino acid sequence has been conservatively substituted. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc. Thus, glycated variants include glycated peptides comprising a variant of the amino acid sequence of Peptides AA-DJ or SEQ ID NOs: 24-36 comprising one or more conservative amino acid substitutions.

Alternatively or additionally, the glycated variants can comprise a variation of the amino acid sequence of the parent glycated peptide (e.g., comprising glycated Peptides AA-DJ or SEQ ID NOs: 24-36), or a glycated fragment thereof, comprising one or more non-conservative amino acid substitution. In this case, it is preferable that the non-conservative amino acid substitution does not interfere with or inhibit the ability of the glycated variant to be detected such that the concentration of the glycated variant represents the concentration of the parent glycated peptide.

Non-limiting examples of glycated variants of the invention include, for instance, a glycated peptide comprising a variant of SEQ ID NO: 6, wherein one or both of the Gln residues at positions 1 and 7 of SEQ ID NO: 6 are replaced with Glu. In this regard, the glycated variant can comprise the amino acid sequence of any of SEQ ID NOs: 37-39. Additionally or alternatively, the glycated variant can comprise a variant of SEQ ID NO: 6, wherein the Glu at position 5 of SEQ ID NO: 6 is replaced with pyroglutamate. In this respect, the glycated variant can comprise the amino acid sequence of any of SEQ ID NOs: 40-43. Similarly, glycated variants of the invention include, for instance, a glycated peptide comprising a variant of SEQ ID NO: 8, wherein the Asn at position 7 of SEQ ID NO: 8 is replaced with Asp. In this regard, the glycated variant can comprise the amino acid sequence of SEQ ID NO: 44. Gycated variants of the invention also include, for instance, a glycated peptide comprising a variant of SEQ ID NO: 9, wherein one or both of the Gln residues at positions 2 and 9 of SEQ ID NO: 9 are replaced with Glu. In this regard, the glycated variant can comprise an amino acid sequence of any of SEQ ID NOs: 45-47. Preferably, the glycated variant comprises an amino acid sequence selected from the group consisting of SEQ ID NOs: 37-47.

The glycated peptides of the invention, as well as glycated fragments and glycated variants thereof, can be of any length, i.e., can comprise any number of amino acids, provided that the peptides (including glycated fragments and glycated variants) are detectable, such that the concentration of the peptides can be ascertained. The glycated peptide, glycated fragment, or glycated variant can, for example, be 5 to 5000 amino acids long, such as 5, 6, 7, 8, 9, 10, 11, 12, 13, 15, 17, 19, 20, 25, 50, 75, 100, 200, 350, 500, 600, 700, 850, 990, 1000, 2225, 3550, 4550, 5000 or more amino acids in length. In this regard, the glycated peptides of the invention, as well as glycated fragments and glycated variants, include glycated polypeptides, glycated oligopeptides, and glycated proteins. In a preferred embodiment, the peptide, fragment, or variant comprises at least 5 amino acids, such that an agent which binds to the glycated peptide, fragment, or variant e.g., an antibody, aptamer, or glucose binding moiety, can bind to the glycated peptide, fragment, or variant in a glycated peptide-specific manner.

The glycated peptides of the invention, as well as glycated fragments and glycated variants thereof, can comprise synthetic amino acids in place of one or more naturally-occurring occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

It is understood that the glycated peptides, and glycated fragments and glycated variants thereof, are glycated, meaning that at least one of the amino acids which make up the peptide contains one or more glucose groups attached thereto. The term "glycated" as used herein refers to the attachment of a sugar molecule (e.g., glucose) to a protein, typically by a non-enzymatic process. Glycation does not encompass N- or O-glycosylation. Typically, the amino acid which is glycated is a lysyl residue, although any other amino acid can be glycated, e.g., Trp, Ala, Arg, Asp, Glu, Gln, Asn, Cys, Phe, Gly, His, Ile, Leu, Met, Pro, Ser, Thr, Val, and Tyr. The glycated amino acid can be found within any region of, i.e., at any position within, the glycated peptide, glycated fragment, or glycated variant. For example, the glycated amino acid can be an amino acid within the amino terminal region of the peptide (e.g., within 50, 40, 30, 25, 10, 5, or 3 amino acids from the N-terminal amino acid). Alternatively, the glycated amino acid can be an amino acid within the carboxy terminal region of the peptide (e.g., within 50, 40, 30, 25, 10, 5, or 3 amino acids from the C-terminal amino acid). The glycated amino acid is, in some cases, preferably the N-terminal amino acid.

The inventive glycated peptides, glycated fragments, and glycated variants can additionally be O-glycosylated, N-glycosylated, amidated, deamidated, carboxylated, phosphorylated, esterified, N-acylated, cyclized via, e.g., a disulfide bridge, or converted into an acid addition salt and/or optionally dimerized or polymerized, or conjugated.

The glycated peptides, glycated fragments, and glycated variants can be in the form of a salt, preferably, a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

The inventive glycated peptides, glycated fragments, and glycated variants can be charged or neutral. If charged, the peptide, fragment, or variant can be of any charge state, e.g., −4, −3, −2, −1, +1, +2, +3, +4, etc.

The glycated peptides of the invention, as well as glycated fragments and glycated variants thereof, can be obtained by methods known in the art, including a two-step method which comprises first obtaining or making the peptide in an unglycated form followed by glycation of the peptide.

Suitable methods of de novo synthesizing peptides (including fragments and variants thereof) are known in the art and are described in references, such as Chan et al., *Fmoc Solid Phase Peptide Synthesis*, Oxford University Press, Oxford, United Kingdom, 2005; *Peptide and Protein Drug Analysis*, ed. Reid, R., Marcel Dekker, Inc., 2000; *Epitope Mapping*, ed. Westwood et al., Oxford University Press, Oxford, United Kingdom, 2000; and U.S. Pat. No. 5,449,752. Also, peptides (including fragments and variants thereof) can be recombinantly produced using nucleic acids which encode the peptides in standard recombinant methods. See, for instance, Sambrook et al., *Molecular Cloning: A Laboratory Manual*, 3rd ed., Cold Spring Harbor Press, Cold Spring Harbor, N.Y. 2001; and Ausubel et al., *Current Protocols in Molecular Biology*, Greene Publishing Associates and John Wiley & Sons, NY, 1994. Further, the glycated peptides, glycated fragments, and glycated variants can be isolated and/or purified from a source, such as a plant, a bacterium, a mammal, e.g., a rat, a human, etc. Methods of isolation and purification are well-known in the art, and include the method described in Example 1. In this respect, the peptides, fragments, and variants of the invention can be synthetic, recombinant, isolated, and/or purified.

Glycation of the synthetic, recombinant, isolated, and/or purified peptides (including fragments and variants thereof) can be carried out by methods known in the art (see, for instance, Heinrikson, *J Biol Chem* 241: 1393-1405 (1966); and Gruber and Hofmann, *J Pept Res* 66: 111-124 (2005)).

The present invention further provides an antibody, or an antigen binding portion thereof, that binds to any of the glycated peptides, or glycated fragments or glycated variants thereof, described herein. The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form. Also, the antibody can have any level of affinity or avidity for the glycated peptide, glycated fragment or glycated variant thereof, of the invention. Desirably, the antibody is specific for the glycated peptide, glycated fragment or glycated variant thereof, such that there is minimal cross-reaction with other peptides or proteins. The antibody can be specific for the glycated amino acid residue, e.g., glycated lysine, and the flanking amino acids of the glycated amino acid residue of a glycated peptide. An antibody of this type is ensured to bind to only glycated peptides, as opposed to unglycated peptides having the same amino acid sequence.

Also, the antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

Suitable methods of making antibodies are known in the art. For instance, standard hybridoma methods are described in, e.g., Köhler and Milstein, *Eur. J. Immunol.*, 5, 511-519 (1976), Harlow and Lane (eds.), *Antibodies: A Laboratory Manual*, CSH Press (1988), and C. A. Janeway et al. (eds.), *Immunobiology*, 5th Ed., Garland Publishing, New York, N.Y. (2001)). Alternatively, other methods, such as EBV-hybridoma methods (Haskard and Archer, *J. Immunol. Methods*, 74(2), 361-67 (1984), and Roder et al., *Methods Enzymol.*, 121, 140-67 (1986)), and bacteriophage vector expression systems (see, e.g., Huse et al., *Science*, 246, 1275-81 (1989)) are known in the art. Further, methods of producing antibodies in non-human animals are described in, e.g., U.S. Pat. Nos. 5,545,806, 5,569,825, and 5,714,352, and U.S. Patent Application Publication No. 2002/0197266 A1).

Phage display furthermore can be used to generate the antibody of the invention. In this regard, phage libraries encoding antigen-binding variable (V) domains of antibodies can be generated using standard molecular biology and recombinant DNA techniques (see, e.g., Sambrook et al. (eds.), *Molecular Cloning, A Laboratory Manual*, 3rd Edition, Cold Spring Harbor Laboratory Press, New York (2001)). Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production or a bacterial cell line, such that antibodies having the characteristics of monoclonal antibodies are secreted by the cell (see, e.g., Janeway et al., supra, Huse et al., supra, U.S. Pat. No. 6,265,150, and Knappik et al., *J. Mol. Biol.* 296: 57-86 (2000).

Antibodies can be produced by transgenic mice that are transgenic for specific heavy and light chain immunoglobulin genes. Such methods are known in the art and described in, for example U.S. Pat. Nos. 5,545,806 and 5,569,825, and Janeway et al., supra.

Methods for generating humanized antibodies are well known in the art and are described in detail in, for example, Janeway et al., supra, U.S. Pat. Nos. 5,225,539, 5,585,089 and 5,693,761, European Patent No. 0239400 B1, and United Kingdom Patent No. 2188638. Humanized antibodies can also be generated using the antibody resurfacing technology described in U.S. Pat. No. 5,639,641 and Pedersen et al., *J. Mol. Biol.*, 235, 959-973 (1994).

Methods of testing antibodies for the ability to bind to any of the glycated peptides, fragments, or variants are known in the art and include any antibody-antigen binding assay, such as, for example, radioimmunoassay (RIA), ELISA, Western blot, immunoprecipitation, and competitive inhibition assays (see, e.g., Janeway et al., supra, and U.S. Patent Application Publication No. 2002/0197266 A1).

The invention also provides antigen binding portions of any of the antibodies described herein. The antigen binding portion can be any portion that has at least one antigen binding site, such as Fab, $F(ab')_2$, dsFv, sFv, diabodies, and triabodies.

A single-chain variable region fragment (sFv) antibody fragment, which consists of a truncated Fab fragment comprising the variable (V) domain of an antibody heavy chain linked to a V domain of a light antibody chain via a synthetic peptide, can be generated using routine recombinant DNA technology techniques (see, e.g., Janeway et al., supra). Similarly, disulfide-stabilized variable region fragments (dsFv) can be prepared by recombinant DNA technology (see, e.g., Reiter et al., *Protein Engineering*, 7, 697-704 (1994)). Antibody fragments of the present invention, however, are not limited to these exemplary types of antibody fragments.

The invention further provides an aptamer that binds to any of the glycated peptides described herein, or glycated fragments or glycated variants thereof. The term "aptamer" as used herein refers to a nucleic acid (e.g., double stranded DNA or single stranded RNA molecule) that binds to a specific molecular target, such as a protein, peptide, or metabolite. Aptamers, as well as methods of making aptamers, are known in the art. See, for example, U.S. Pat. Nos. 5,475,096; 5,270,163; 6,974,706, and 5,656,739, as well as International Patent Application No. WO 91/19813.

The aptamer can be chemically synthesized using naturally occurring nucleotides or modified nucleotides designed to increase the biological stability of the molecule or to increase the physical stability of the duplex formed upon hybridization (e.g., phosphorothioate derivatives and acridine substituted nucleotides). Examples of modified nucleotides that can be used to generate the aptamers include, but are not limited to, 5-fluorouracil, 5-bromouracil, 5-chlorouracil, 5-iodouracil, hypoxanthine, xanthine, 4-acetylcytosine, 5-(carboxyhydroxymethyl)uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), butoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, (acp3) w, and 2,6-diaminopurine. Also, the aptamer can contain a natural, non-natural or altered internucleotide linkage, such as a phosphoroamidate linkage or a phosphorothioate linkage, instead of the phosphodiester found between the nucleotides of an unmodified oligonucleotide.

Furthermore, the aptamers described herein can be modified to comprise a detectable label, such as any of those described herein.

Also provided by the invention is a conjugate comprising (i) an antibody, antigen binding portion thereof, or aptamer which specifically binds to a peptide, or fragment or variant thereof, comprising (a) at least one of Peptides AA-DJ or (b) an amino acid sequence selected from the group consisting of SEQ ID NOs: 24-36, and (ii) a detectable label. The conjugate can further comprise a glucose binding moiety. The glucose-binding moiety can be any moiety that will bind specifically to a glucose molecule, such as an antibody, a lectin, or a borate. The antibody, antigen-binding portion thereof, or aptamer can be any antibody, antigen binding portion thereof or aptamer that specifically binds to a peptide, or a fragment or variant thereof, comprising (a) at least one of Peptides AA-DJ or (b) an amino acid sequence selected from the group consisting of SEQ ID NOs: 24-36. The peptide to which the antibody, antigen-binding portion thereof, or aptamer binds can be glycated or unglycated. In the instance that the peptide to which the antibody, antigen-binding portion thereof, or aptamer binds is unglycated, it is preferable for the detectable label to be detected only when the antibody, antigen-binding portion thereof, or aptamer binds to the peptide and the glucose-binding moiety binds to a glucose molecule(s) attached to the peptide. A conjugate of this type is ensured to be detectable only when bound to glycated peptides, as opposed to unglycated peptides having the same amino acid sequence. The detectable label can be any detectable label, such as any of those described herein. Conjugates, as well as methods of synthesizing conjugates, are known in the art (See, for instance, Hudecz, F., *Methods Mol Biol* 298: 209-223 (2005) and Kirin et al., *Inorg Chem* 44(15): 5405-5415 (2005)).

The inventive glycated peptides, glycated fragments, and glycated variants thereof, antibodies, antigen binding portions, aptamers, and conjugates can be isolated and/or purified. The term "isolated" as used herein means having been removed from its natural environment. The term "purified" as used herein means having been increased in purity, wherein "purity" is a relative term, and not to be necessarily construed as absolute purity. For example, the purity can be at least 50%, can be greater than 60%, 70% or 80%, or can be 100%.

The glycated peptides (including glycated fragments and glycated variants thereof), antibodies (including antigen binding portions thereof), aptamers, and conjugates described herein can be formulated into a composition, such as a pharmaceutical composition. In this regard, the invention provides a composition comprising any of the glycated peptides (including glycated fragments and glycated variants thereof), antibodies (including antigen binding portions thereof), aptamers, and conjugates, and a carrier, especially a pharmaceutically acceptable carrier. The inventive composition can further comprise more than one of any of the glycated peptides (including glycated fragments and glycated variants thereof), antibodies (including antigen binding portions thereof), aptamers, and conjugates of the invention (e.g., a glycated peptide and an antibody that specifically binds to a glycated peptide, or two or more different glycated peptides, such as Peptides AA and AB). Alternatively or in addition, the composition can comprise a pharmaceutically active agent or drug (e.g., an anti-diabetic drug) or another agent that can be used to monitor glycemic control (e.g., an antibody specific for HbA1C).

The inventive glycated peptides (including glycated fragments and glycated variants thereof), antibodies (including antigen binding portions thereof), aptamers, conjugates, and compositions described herein can be used for any purpose. As the glycated peptides (including glycated fragments and glycated variants thereof) of the invention have been associated with glycemic control and diabetes, the foregoing compounds and compositions described herein are especially useful in connection with methods to research, monitor, detect, treat, or prevent diabetes. Such methods may comprise in vivo or in vitro use of such compounds or compositions. Certain methods involving the use of these compounds and compositions are described in greater detail herein; however, the described methods do not limit the utility of the foregoing compounds and compositions.

As previously mentioned, the glycated peptides, and glycated fragments and glycated variants, described herein have been associated with glycemic control and diabetes. More specifically, the concentration of the glycated peptides, and glycated fragments and variants thereof, can be increased in diabetic patients as compared to non-diabetic patients, thereby suggesting that these glycated peptides, and glycated fragments and glycated variants thereof, can be used as markers or indices of glycemic control. In this regard, the invention provides a method of monitoring glycemic control of a host comprising measuring the concentration of a glycated peptide, or a glycated fragment or glycated variant thereof, in a host, wherein the glycated peptide comprises (i) at least one of Peptides AA-DJ or (ii) an amino acid sequence of the group consisting of SEQ ID NOs: 24-36.

The term "concentration" as used herein encompasses absolute concentration as well as relative concentration. Typically, the methods described herein will be performed using relative concentrations. Relative concentration, in this regard, is the concentration of a molecule, compound, or substance (e.g., a glycated peptide) as compared to the concentration of a total population of molecules, compounds, or substances of which the molecule, compound, or substance of interest is a part (e.g., the total population of a given peptide in both glycated and non-glycated forms), or as compared to the concentration of a different molecule, compound, or substance (e.g., the non-glycated form of the same peptide). Thus, the relative concentration of a glycated peptide, fragment or variant can indicate a percentage of the total population of the given peptide, fragment, or variant in a sample that is in its glycated form. Alternatively, the relative concentration of a glycated peptide, fragment, or variant can indicate a ratio of glycated to non-glycated forms of the give peptide, fragment, or variant.

The term "glycemic control" as used herein does not refer to the level of blood glucose in a host taken at a particular point in time, as blood glucose levels vary throughout the day and fluctuate as a function of, for example, food intake by the host. Rather, "glycemic control" refers to the blood glucose level in a host over a period of time, e.g., a day, a week, a month, etc. Glycemic control also can be described as the area under a curve formed by plotting the minute-to-minute changes in blood glucose levels in a host over a given time period. The glycemic control of a host is considered "normal" or "good" when the blood glucose levels of a host (as represented, e.g., by the area under a glycemic control curve) are the same or nearly the same as the blood glucose levels of a "normal" or non-diabetic host (or a population of such normal or non-diabetic hosts) over a given time frame. In contrast, the glycemic control of a host can be described as "abnormal" or "poor" when the blood glucose levels of that host (as represented, e.g., by the area under a glycemic control curve) are different from the blood glucose levels of a "normal" or non-diabetic host (or a population of such normal or non-diabetic hosts) over a given time frame. Abnormal or poor glycemic control is typically indicated by abnormally elevated blood glucose levels in the case of diabetes, but also can be indicated by abnormally depressed blood glucose levels when certain conditions exist (e.g., an insulin-secreting tumor).

Although glycemic control reflects blood glucose levels over a period of time, the term "monitoring glycemic control of a host" does not necessarily involve making multiple measurements of blood glucose levels at different points in time. As previously mentioned with respect to HbA1C, a measurement of the concentration of a glycated peptide reflects a history of blood glucose levels over time. Thus, even a single measurement of a glycated peptide concentration can be informative of the history of glycemic control. Accordingly, monitoring glycemic control can comprise, for instance, taking a single measurement of a concentration of a glycated peptide in a host. Of course, monitoring glycemic control can comprise taking two or more measurements (e.g., three, five, eight, or more measurements) at different time points.

As used herein, the term "diabetes" refers to any type or stage of diabetes, including, but not limited to, Type 1 diabetes, Type 2 diabetes, diabetes mellitus, juvenile-onset diabetes, adult-onset diabetes, non-insulin-dependent diabetes, insulin-dependent diabetes, sugar diabetes, gestational diabetes, prediabetes, and other conditions associated with elevated glucose levels or impaired glycemic control including, without limitation, impaired glucose tolerance; impaired fasting glucose; pancreatic diabetes (e.g., from pancreatectomy), chronic pancreatitis, and hemochromatosis.

Improved glycemic control, i.e., maintenance of blood glucose levels at normal or non-diabetic levels, is a major goal of current diabetes therapy, and improved glycemic control has been shown to prevent or delay the onset of long-term diabetic complications in both Type 1 and Type 2 diabetic patients. In this regard, the invention further provides a method of preventing or treating diabetes, including any complication or symptom of diabetes, which method comprises monitoring the glycemic control of a host as described herein.

The terms "treat" and "prevent" as well as words stemming therefrom, as used herein, do not necessarily imply 100% or complete treatment or prevention. Rather, there are varying degrees of treatment or prevention. In this respect, the inventive method of treating or preventing diabetes can provide any level of treatment of diabetes in a host, including without limitation the reduction to any degree of any one or more symptoms or complications of diabetes. Similarly, the inventive method of treating or preventing diabetes can provide any level of prevention, including without limitation delaying the onset of any one or more symptoms or complications of diabetes.

As used herein, "symptom of diabetes" or "complication of diabetes" refers to a secondary condition that often occurs in diabetic patients due to the hyperglycemia of diabetes, and includes, for instance, microvascular complications (diseases of small blood vessels, e.g., retinopathy, neuropathy, nephropathy), macrovascular complications (diseases of large blood vessels, e.g., coronary heart disease, atherosclerosis of other blood vessels, intermittent claudication, peripheral vascular disease, etc.), blindness (which is caused by diabetic retinopathy and other retinal disorders), kidney failure (which is caused by diabetic nephropathy), foot wounds, ulcers, foot and leg amputations (which are caused by diabetic peripheral vascular disease and/or diabetic neuropathy), paralysis of the stomach (also known as gastroparesis), chronic diarrhea, inability to control heart rate and blood pressure with posture changes, heart attack, stroke, peripheral vascular disease, and a predisposition to high blood pressure and high cholesterol and triglyceride levels.

The method of monitoring glycemic control by measuring the concentration of the inventive glycated peptides, or glycated fragments or glycated variants thereof, can be used to detect abnormal glycemic control and, thus, monitor or detect the onset, progression, or regression of diabetes. In this respect, the invention further provides a method of monitoring or detecting the onset, progression, or regression of diabetes in a host. The method comprises monitoring the glycemic control of a host as described herein, or, more particularly, detecting a change in glycemic control of a host. A change in the glycemic control of the host can be detected on the basis of a change in the concentration of a glycated peptide, or glycated fragment or glycated variant thereof, wherein a decrease in the concentration of a glycated peptide, or glycated fragment or glycated variant thereof, is indicative of a regression of diabetes in the host and an increase in such concentration is indicative of the onset or progression of diabetes in the host.

The change in concentration of a glycated peptide, or glycated fragment or glycated variant thereof, is typically a change in concentration relative to an earlier measured concentration of the same glycated peptide, or glycated fragment or glycated variant thereof, in the same host at a different point in time. However, a change in the concentration of the glycated peptide, or glycated fragment or glycated variant thereof, also can be detected by comparison to a control, such as the concentration of the same glycated peptide, or glycated fragment or variant thereof, in a known non-diabetic or diabetic patient. The control also can be provided by a standard profile or index of the concentrations of the glycated peptide, or glycated fragment or glycated variant thereof. Such a profile or index can reflect the relevant concentrations the glycated peptide, or glycated fragment or glycated variant thereof, in a population of known non-diabetic or diabetic patients.

The methods described herein also can be used to evaluate the effectiveness of a course of treatment in a host. For instance, the concentration of one or more of the glycated peptides, or glycated fragments or glycated variants thereof, can be measured before and after the administration of a treatment for diabetes and the concentration levels compared. If the concentration of one or more of the glycated peptides, or glycated fragments or glycated variants thereof, measured after treatment is lower than the concentration of the same glycated peptides, or glycated fragments or glycated variants thereof, before treatment, then the treatment would be deemed relatively effective. If the concentration of one or more of the glycated peptides, or glycated fragments or glycated variants thereof, measured after treatment is higher than or the same as the concentration of the glycated peptides, or glycated fragments or glycated variants thereof, measured before treatment, then the treatment would be deemed relatively ineffective. In this regard, the invention also provides a method of determining the efficacy of a diabetes treatment. The method comprises monitoring glycemic control in a host, as described herein, before, during, and/or, after the administration of a diabetes treatment.

The diabetes treatment can be any treatment, therapy, or regimen which is designed to counter diabetes or a symptom or condition thereof. The diabetes treatment can be, for example, a medication designed to treat diabetes, e.g., a sulfonylurea, a biguanide, an α-glucosidase inhibitor, a thiazolidinedione, a meglitinide, a D-phenylalanine derivative, an amylin synthetic derivative (e.g., pramlintide), an incretin mimetic (e.g., exenatide), and an insulin (e.g., a rapid-acting insulin (e.g., HUMULIN R, NOVOLIN R, HUMALOG, NOVOLOG, APIDRA, SEMILENTE), an intermediate-acting insulin (e.g., HUMULIN R, NOVOLIN R), a long-acting insulin (e.g., ULTRALENTE, LANTUS, LEVEMIR), and the like. The diabetes treatment can be a specific regimen of a drug, e.g., a once, twice, or thrice daily regimen of insulin injections.

The invention also provides a method of detecting diabetes or a predisposition to diabetes in a host. The method can comprise monitoring the glycemic control of the host as described herein. More particularly, the method can comprise detecting in the host an elevated concentration of a glycated peptide, or a glycated fragment or glycated variant thereof, as compared to a control, wherein the glycated peptide comprises (i) at least one of Peptides AA-DJ or (ii) an amino acid sequence of the group consisting of SEQ ID NOs: 24-36. Detection of an elevation in the concentration of the glycated peptide, or a glycated fragment or glycated variant thereof, is indicative of diabetes or a predisposition to diabetes in the host. While any elevation in the concentration of the glycated peptide, or glycated fragment or glycated variant thereof, can be indicative of diabetes or a predisposition to diabetes, the elevation is preferably a statistically significant elevation as compared to a control. Suitable controls are as described elsewhere herein. A preferred control can be an profile or index based on concentrations of the relevant glycated peptides, or fragments or variants thereof, from a population of known diabetic or non-diabetic hosts. Statistical significance can be represented by a low P value, such as a P value of 0.05 or less, 0.01 or less, 0.005, or less, or 0.001 or less. In a preferred embodiment, the P value is 0.001 or less. Of course, in practice, the statistical significance of any given elevation in concentration can be incorporated into the control or index that is chosen as appropriate for the particular application.

Any of the methods described herein can comprise any number of additional steps. The methods can, for instance, further comprise comparing the concentration of the glycated peptide, or glycated fragment or glycated variant thereof, to a control. Comparison to a control allows, for example, the detection of an elevated level of a glycated polypeptide, or glycated fragment or glycated variant thereof, which can indicate abnormal glycemic control or diabetes. Suitable controls are as described herein with respect to other aspects of the invention. Furthermore, the methods described herein can comprise comparing two or more measurements of the concentration of a glycated peptide, or glycated fragment or glycated variant thereof, taken from the same host at different points in time. Such a comparison allows, for instance, the detection of a change in the concentration of a glycated peptide, or glycated fragment or glycated variant thereof, which change can indicate a change in the glycemic control of the host, the onset, progression, or regression of diabetes in a host, or the effectiveness of a diabetes treatment in a host.

The inventive methods can further comprise measuring a concentration of HbA1C protein and/or the blood glucose level of the host. Methods of measuring the concentration of HbA1C and/or blood glucose levels are known in the art.

The concentration of one or more glycated peptides, or glycated fragments or glycated variants thereof, in a host can be measured in a sample of the host, i.e., a sample obtained directly from the host, optionally subject to further processing, or a sample derived from the host. The sample can be any sample from the host, including, but not limited to whole blood, blood plasma, or blood serum. Alternatively, the measurement can be taken directly within the host, such as by using a radio-labeled antibody which specifically binds to a glycated peptide or fragment or variant thereof, as described herein.

Suitable methods of measuring the concentration of a peptide (e.g., a glycated peptide, or glycated fragment or glycated variant thereof) in a sample or host are known in the art. For instance, the concentration of a glycated peptide, or glycated fragment or glycated variant thereof, can be measured by mass spectrometry (MS), high performance liquid chromatography (HPLC), or both MS and HPLC. Alternatively or in addition, the concentration of a glycated peptide, or glycated fragment or glycated variant thereof, can be measured indirectly, for example, by contacting the sample with an antibody, antigen binding portion thereof, aptamer, conjugate, or other detectable binding agent that specifically binds to the glycated peptide or glycated fragment or glycated variant thereof, and thereafter measuring the concentration of bound (e.g., complexed) antibody, antigen binding portion thereof, aptamer, conjugate, or other detectable binding agent. Methods of quantifying the concentration of a bound antibody, antigen binding portion, aptamer, or conjugate are known in the art and include, for instance, quantitative western blotting (e.g. western blotting followed by phosphorimaging or scintillation counting), solution-based immunoassays (e.g., ELISA, immunoprecipitation, radioimmunoassay), mass spectrometry, and HPLC.

The concentration of the glycated peptide, or glycated fragment or glycated variant thereof, also can be measured on the basis of the specific activity or biological activity of the protein of which the glycated peptide, fragment, or variant is a part. Such proteins are described herein. Without wishing to be bound to any particular theory, it is believed that glycation alters the mass and, in some instances, the biological activity of the protein. Accordingly, the specific activity and, perhaps, the enzyme activity of a sample of the protein will be changed if a high relative concentration of the glycated form of the protein is present. This change in the specific activity or biological activity of the protein, thus, can serve as an indirect measure of the concentration of the glycated peptide, or glycated fragment or variant thereof. Alternatively, a change in the specific activity or biological activity of the protein can, itself, serve as a basis for monitoring glycemic control. In this regard, the inventive method of monitoring glycemic control can comprise measuring or detecting a change in the biological activity or specific activity of a glycated protein, wherein the glycated protein comprises (i) at least one of Peptides AA-DJ or (ii) an amino acid sequence selected from the group consisting of SEQ ID NOs: 24-36.

In this regard, the term "specific activity" refers to the biological activity (e.g., enzyme activity) of a protein divided by its mass. The term "biological activity" refers to any natural function of a protein, including, for example, enzyme activity, binding affinity, activating activity, inhibitory activity, etc. A change in the specific activity or biological activity of the protein can be detected by comparing the specific activity or biological activity of the protein in a sample to a suitable control, such as the specific activity or biological activity of the same protein in a known "normal" or "abnormal" sample, or a standardized or otherwise accepted value of the specific activity or biological activity known in the art.

In order to determine a relative concentration of a glycated peptide, or glycated fragment or glycated variant thereof, as previously described herein, it is necessary to determine the concentration of the non-glycated peptide, fragment, or variant, or the concentration of the total population of both glycated and non-glycated forms of the relevant peptide, fragment, or variant. The concentration of the non-glycated peptide, fragment, or variant, or the concentration of the total population of glycated and non-glycated forms of the relevant peptide, fragment, or variant, can be determined by any method of measuring a concentration of a peptide or protein known in the art. The method of measuring the total concentration can be the same or a different method used to determine the concentration of the corresponding glycated peptide, fragment, or variant, including methods previously described herein with obvious modifications (e.g., without enriching the sample for glycated peptides, or without removing non-glycated peptides). For example, MS or HPLC can be used to determine the concentration of both the non-glycated and glycated forms of the peptide, fragment, or variant. Alternatively, MS can be used to determine the total concentration, while HPLC is used to determine the concentration of the glycated peptide. Also, an antibody- or aptamer-based method can be used to measure or determine the concentration of the non-glycated and glycated forms of a given peptide, fragment, or variant. The antibody or aptamer used to detect the non-glycated forms of the peptide can be a different antibody or aptamer than the antibody or aptamer used to detect the glycated peptide. For instance, the antibody or aptamer used to determined the concentration of the glycated peptide can be specific for the glycated form of that peptide, such that it would not detect the unglycated form of the peptide, and a different antibody or aptamer that detects only the non-glycated form of the peptide, or that detects both non-glycated and glycated forms of the peptide, can be used to determine the concentration of the non-glycated peptide or total population of the peptide in both non-glycated and glycated forms.

With respect to the inventive methods, the glycated peptide, or glycated fragment or glycated variant thereof, can be any of those described herein. In a preferred embodiment, the glycated fragment comprises an amino acid sequence of any of peptides AA-DJ, e.g., an amino acid sequence selected from the group consisting of SEQ ID NOs: 1-23. In another preferred embodiment, the methods comprise detecting or measuring the concentration of a glycated variant comprising an amino acid sequence selected from the group consisting of SEQ ID NOs: 37-47.

Further, with respect to the inventive methods, the methods can comprise measuring the concentration of two or more different glycated peptides, glycated fragments, and/or glycated variants, as described herein. For instance, the method can comprise measuring the concentration of 3, 4, 5 or more different glycated peptides or glycated fragments thereof, or even measuring the concentration of 6, 7, 8, 9, 10, 20, 35, 45, 50, 75 or more different glycated peptides or glycated fragments thereof, as described herein. The method can comprise measuring the concentration of each of Peptides AA-DJ, and of SEQ ID NOs: 37-47.

The term "host" as used herein refers to any eukaryotic host in which glycemic control can be monitored. The host can be, for instance, a bird, a reptile, or a mammal. As used herein, the term "mammal" refers to any mammal, including, but not limited to, mammals of the order Rodentia, such as mice and hamsters, and mammals of the order Logomorpha, such as rabbits. It is preferred that the mammals are from the order Camivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human. Any of the foregoing methods described herein can be performed in conjunction with any of the above-described hosts.

The invention further provides a database comprising data which indicates the concentration, preferably the relative concentration, of one or more of the glycated peptides described herein, or glycated fragments or glycated variants thereof, that is present in diabetic patients, non-diabetic patients, or both diabetic and non-diabetic patients. The data additionally can be indicative of a stage or level of severity of diabetes. The term "database" as used herein means a collection of data, and does not imply any particular format for the data. Thus, the database can be an electronic database, e.g., a computerized database, wherein data can be easily stored, queried, added, edited, deleted, updated, and/or organized. Alternatively, the data can be compiled in a non-electronic form (e.g., on paper or other suitable substrate). Regardless of whether the database is an electronic database or a non-electronic database, the data can be formatted as an index, chart, graph, or text. The database can be used for any purpose, but is particularly useful in conjunction with methods of researching, monitoring, screening, detecting, and diagnosing glycemic control, diabetes, and any symptom or complication thereof. Such methods include, but are not limited to, the methods described herein. In this regard, the database can be used, for example, as the control referred to in the methods described herein.

The database can be created by any suitable method, such as by measuring the relative concentration of one or more of the glycated peptides, or glycated fragments or variants thereof, as described herein, in a population of known diabetic or non-diabetic persons and compiling the data. Optionally, known statistical techniques can be employed, for example, to establish the significance of any variation in measurements between individuals in the population. Of course, the population can be further refined to include categories of diabetic or non-diabetic persons, for example, based on the type or level of severity of diabetes present. Suitable methods for determining the appropriate population size and type needed to establish a database of statistical significance are within the skill of the ordinary artisan.

The invention further provides a kit comprising one or more of the antibodies, or antigen binding fragments, aptamers, and/or conjugates described herein, or one or more glycated peptides, or glycated fragments or glycated variants thereof, as described herein. The kit can further comprise additional agents or materials, such as an agent used to measure other indices of glycemic control, for example, an agent which measures blood glucose level and/or an agent which measures the level of a glycated HbA1C protein. Additionally or alternatively, the kit can comprise (a) a reagent for the detection of a glycated peptide, antibody, antigen binding fragment, aptamer, or conjugate included in the lit, (b) a standard for determining the molecular weight or specific activity of a glycated peptide, or glycated fragment or glycated variant thereof (or the protein such peptide is derived from), (c) a database as described herein, or (d) a set of user instructions as to how to use the kit or any part thereof, especially for purposes consistent with the methods disclosed herein.

EXAMPLES

The following examples further illustrate the invention but, of course, should not be construed as in any way limiting its scope.

Example 1

This example demonstrates that elevated concentrations of Peptides AA-DJ, as well as the proteins of which some of the peptides are a part, are indicative of poor glycemic control and can be used to detect a diabetic condition.

All chemicals and biochemicals were purchased from Sigma-Aldrich, St. Louis, Mo., if not specified otherwise.

Plasma samples were obtained from nine diabetic patients with a hemoglobin A1C (HbA1C) concentration of greater than 14%, and from nine non-diabetic patients with an HbA1C concentration of less than 6%. The samples were thawed at 4° ° C. for 4 hours. 175 µl aliquots from each sample were subjected to an antibody affinity column (Agilent, Palo Alto, Calif.) to remove the six most abundant serum proteins: albumin, IgG, IgA, haptoglobin, transferrin, and antitrypsin proteins. Affinity column processing was carried out with 35 µl of plasma per run. The volume of each processed aliquot was then adjusted to about 100 µl using ultracentrifugation spin columns with 5 kDa molecular-weight cutoff (Millipore, Billerica, Mass.).

Each 100 µl aliquot was diluted with 1.0 mL of 6M guanidium hydrochloride, 100 mM Tris (pH 8.0). Dithiothreitol (DTT, Cleland's reagent) was then added to a final concentration of 10 mM. The aliquots were subsequently incubated at 37° ° C. for 4 hours. After allowing the aliquots to cool to room temperature, 25 µl of 1.0 M iodoacetic acid in 1.0 M sodium hydroxide was added and the mixture was incubated at room temperature for 30 minutes. The buffer condition of the mixture was then changed to 50 mM $NH_4HCO_2$ (pH 8.3) via centrifugation with ultracentrifugation spin columns, as described above.

After changing the buffer condition, modified trypsin (Promega, Madison, Wis.) was added to each aliquot at a weight ratio of 1:50 and digestion was carried out at 37° C. for 16 hours. The resulting tryptic peptides were desalted on a RapidTrace™ workstation (Caliper, Mountain View, Calif.) using C18 reversed phase cartridges (200 mg capacity, Waters, Milford, Mass.). The tryptic peptides were vacuum dried and then dissolved in buffer provided with a glycanase kit (Glyco® kit from Prozyme, San Leandro, Calif.) for deglycosylation. The tryptic peptide solution was treated at 37° C. overnight with a mixture of five glycanases: N-Glycanase, non-specific neuraminidase, O-glycosidase, beta-galactosidase, and beta-N-acetylhexosaminidase (Prozyme, San Leandro, Calif.). Free glycans were removed from the tryptic peptide mixture by C18 purification followed by lyophilization. The lyophilized mixture was dissolved in ammonium acetate (200 µl of 0.2 M solution at pH 8.8).

In order to enrich the tryptic peptide mixture for glycated peptides, the tryptic peptide mixture was incubated with 100 µl m-aminophenylboronic acid beads (Pierce, Rockford, Ill.) at room temperature for 15 minutes and the supernatant containing the non-glycated tryptic peptides was removed. The m-aminophenylboronic acid beads were then washed twice with 40% acetonitrile, 60% 0.2 M ammonium acetate (pH 8.2), and the glycated peptides were eluted from the beads with 0.4% formic acid in water. The supernatant was subsequently lyophilized.

The lyophilized glycated peptide mixture was dissolved in 20 μl 0.1% formic acid and analyzed by liquid chromatography-mass spectrometry (LC-MS). Those ions with significant quantitative differences at the p<0.001 level, or that were found only in the diabetic samples and not in the control samples, provided the m/z values used for targeted identification.

Of the 627 glycated tryptic peptides analyzed, the mean concentrations of 88 peptides (Peptides AA-DJ) were significantly greater in the samples from the diabetic patients than from controls (P<0.05). 71 of the 88 peptides had increased mean concentrations in the diabetic samples as compared to the controls with a statistical significance of P-value<0.001, and 79 of the 88 peptides peptides had increased mean concentrations in the diabetic samples as compared to the controls with a statistical significance of P-value<0.005, and 82 of the 88 peptides exhibited increased mean concentrations in the diabetic samples as compared to the controls with a statistical significance of P-value<0.01. The fold-change of each of glycated peptides AA-DJ in diabetic as compared to non-diabetic patients, along with the corresponding P-value, is provided in Table 1.

Only ten peptides of the 7929 total peptides (glycated and non-glycated peptides) found in the un-enriched fractions of the samples exhibited a significantly greater concentration in diabetic samples as compared to control samples (P<0.001). This suggests the importance of enriching the glycated peptides by treatment of m-amino phenylboronic acid.

Table 3 shows the fold increase in mean concentration of nine of Peptides AA-DJ having most significant fold-increase in the diabetic samples as compared to the control samples, as well as the fold increase in HbA1C in diabetic as compared to the control samples. As shown in Table 3, the elevation in these peptides was greater than the elevation in mean concentration of HbA1C. These results suggest that the glycated peptides identified herein might provide more sensitive indices of glycemic control than HbA1C.

TABLE 3

| Peptide | Fold increase in diabetic samples vs. control samples | P value |
| --- | --- | --- |
| HbA1C | 2.8 | $10^{-8}$ |
| AA | 6.0 | $10^{-12}$ |
| AB | 7.8 | $10^{-11}$ |
| AC | 7.4 | $10^{-10}$ |
| AD | 6.7 | $10^{-10}$ |
| AE | 7.1 | $10^{-9}$ |
| AF | 8.2 | $10^{-9}$ |
| AG | 7.5 | $10^{-9}$ |
| AH | 8.0 | $10^{-8}$ |
| AI | 8.4 | $10^{-8}$ |

For some of Peptides AA-DJ, the amino acid sequences were determined by conducting ion-trap mass spectrometry on a Thermo Electron Corp, LTQ spectrometer (San Jose, Calif.) (Table 1). Initial attempts to identify the peptides involved performing $MS^3$ analysis on the $[M-3H_2O]^{n+}$ neutral-loss ion that was frequently the most intense ion present in the $MS^2$ scan. This was only partially effective and it was found that, in many cases, the $MS^3$ spectrum produced only a fourth loss of a water molecule without clear peptide backbone fragmentation. Further identification attempts used a different neutral-loss ion to perform the $MS^3$ analysis. The neutral loss ion $[M-84]^+$, corresponding to the loss of three water molecules plus formaldehyde, was found to be much more likely to undergo observable peptide backbone fragmentation and therefore was used as the precursor for $MS^3$ scans in targeted identification analyses. Database searches using the Mascot software (Matrix Sciences, London, UK) were performed on resulting $MS^3$ spectra using a variable modification on lysine of +78 Daltons. As shown in Table 2, the sequences of these peptides were found to be part of larger plasma proteins.

This example demonstrates that peptides comprising glycated Peptides AA-DJ are markers of abnormal glycemic control and a diabetic condition.

Example 2

This prophetic example demonstrates a method of making antibodies to some of glycated Peptides AA-DJ.

Five or more of glycated Peptides AA-DJ are synthesized as described in Gruber and Hofmann, *J Pept Res* 66: 111-124 (2005). Non-glycated forms of the glycated peptides also are made using conventional peptide synthesis methods (see, for example, Chan et al., *Fmoc Solid Phase Peptide Synthesis*, Oxford University Press, Oxford, United Kingdom, 2005). Antibodies specific for the synthesized glycated and non-glycated peptides are made using conventional immunization techniques and/or display selection techniques (Blaydes et al, *Methods Mol Biol* 99: 177-189 (2000)).

Antibodies to the glycated peptides are tested for selectivity for the glycated peptides over the corresponding non-glycated peptides. The relative sensitivity and specificity for the glycated peptide-specific antibodies are evaluated by conventional western blotting techniques using stored plasma samples from anonymous subjects with varying degrees of glycemic control. The glycated peptide-specific antibodies also are tested against commercially available antibodies which bind to the plasma proteins of which the glycated peptides are a part. Antibodies having high selectivity for the glycated peptides are isolated.

This example demonstrates a method of making antibodies to the inventive glycated peptides described herein.

Example 3

This prophetic example demonstrates a method of creating a database in the form of an index showing the normal and abnormal levels of glycation for one or more glycated peptides present in both diabetic and non-diabetic persons. The example further demonstrates a method of detecting diabetes in a host, a method of determining the efficacy of a diabetes treatment, a method of monitoring the progression or regression of diabetes in a host, and a method of monitoring glycemic control in a host.

Plasma samples are obtained from a population of diabetic patients known to have "poor" or abnormal glycemic control, and from a population of non-diabetic patients known to have "good" or normal glycemic control. The population of diabetic patients is further subdivided into patients known having moderately poor glycemic control and those having severely poor glycemic control.

The concentrations of glycated peptides of Peptides AA-DJ are determined using the antibodies produced by the method of Example 2 in quantitative western blotting using chemiluminescence imaging. The total concentrations of the same peptides, including glycated and non-glycated forms of the peptides, are determined in parallel using commercially available antibodies that identify the peptides regardless of glycation. The relative concentration of the glycated peptides is calculated by dividing the concentration of a given glycated peptide by the total concentration of the same peptide in both glycated and non-glycated forms. The results are averaged within each population, and the average relative concentration for each glycated peptide is recorded into a computerized database and classified as "normal," "moderately poor," and "severely poor." The computerized database is formatted as an index showing ranges of the relative concentrations of the assayed glycated peptides that fall within the above classifications.

Patient Smith, who has a family history of diabetes, does not know if he is currently diabetic and visits his doctor to determine whether or not he is diabetic. A blood sample from Patient Smith is assayed to determine the relative concentrations of certain glycated peptides of Peptides AA-DJ. The assay is performed using an immunoassay kit comprising antibodies and aptamers that bind to certain glycated peptides of Peptides AA-DJ, and a reagent for detecting the bound aptamers and antibodies.

The results show the percentage of the population of an assayed peptide or collection of peptides that are glycated. The percentage is compared to the above-described index to obtain a result of "normal," "moderately poor," or "poor." Patient Smith's test is rated as "poor."

Based on the above results and, perhaps, the results of other tests, Patient Smith's doctor prescribes a regimen of insulin injections. Patient Smith adheres to the prescribed regimen for 3 months and returns to the doctor for a follow-up visit. A blood sample from Patient Smith is again assayed for the relative concentrations of certain glycated peptides of Peptides AA-DJ and the result scored using the index as described above. Based on the comparison, Patient Smith's test is scored as "moderate," indicating an improvement in his glycemic control and the efficacy of the prescribed treatment.

Example 4

This prophetic example demonstrates a method of monitoring the efficacy of treatment of diabetic patients.

The fraction of glycated HbA1C (as compared to the concentration of total hemoglobin A) in a patient who was newly diagnosed with diabetes was monitored during a course of 16 weeks of intensive diabetes treatment. The fraction of glycated HbA1C (as compared to the concentration of total hemoglobin A) was found to decrease two-fold, suggesting that the treatment was effective in treating the diabetes in the patient.

The relative concentration of one or more of the glycated Peptides AA-DJ (as compared to the concentration of both glycated and non-glycated form of the corresponding peptide) in a patient undergoing treatment for diabetes is measured before, during, and after administration of the diabetes treatment. It is expected that the concentration of a glycated peptide decreases upon effective treatment of diabetes in the patient.

This example demonstrates monitoring the efficacy of treatment of diabetic patients based on the relative concentration of Peptides AA-DJ.

Example 5

This prophetic example demonstrates that the method of monitoring glycemic control according to the invention is more sensitive that methods based on HbA1C levels.

Plasma is obtained from subjects with HbA1C levels within or near the normal range, but who nonetheless have mild abnormalities of either glucose tolerance, as determined by either a two hour oral glucose tolerance test, or a slightly elevated fasting plasma glucose. The concentration of glycated Peptides AA-DJ (as compared to the concentration of the unglycated peptides) in these subjects is compared to HbA1C levels. It is expected that the concentrations of some of glycated Peptides AA-DJ will differ from control values more dramatically among these subjects than the concentrations of HbA1C.

This example demonstrated that certain glycated peptides will fluctuate in concentration more dramatically and possibly more rapidly than HbA1C, thereby providing better glycemic control indices.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of monitoring the glycemic control of a host, comprising
   (a) measuring the concentration of a glycated peptide in the host or in a sample from the host, wherein the glycated peptide comprises (i) at least one of Peptides AA-DJ of Table 1 or (ii) an amino acid sequence selected from the group consisting of SEQ ID NOs: 24-36, and
   (b) comparing the measured concentration to a control to determine whether the measured concentration in the host or sample from the host differs from the control.

2. The method of claim 1, further comprising detecting a change in the concentration of the glycated peptide, or glycated fragment or glycated variant thereof.

3. The method of claim 1, further comprising comparing the concentration of the glycated peptide, or glycated fragment or glycated variant thereof, to a control.

4. The method of claim 1, wherein the concentration of the glycated peptide, or glycated fragment or glycated variant thereof, is the relative concentration of the glycated peptide, or glycated fragment or glycated variant thereof, as compared to the total concentration of both the glycated and non-glycated forms of the corresponding peptide; fragment, or variant.

5. The method of claim 1, wherein the glycated fragment comprises an amino acid sequence selected from the group consisting of SEQ ID NOs: 1-23.

6. The method of claim 1, wherein the glycated variant comprises an amino acid sequence selected from the group consisting of SEQ ID NOs: 37-47.

7. The method of claim 1, comprising measuring the concentration of five or more different glycated peptides, or glycated fragments or glycated variants thereof, each of which comprises (i) at least one of Peptides AA-DJ of Table 1 or (ii) an amino acid sequence selected from the group consisting of SEQ ID NOs: 24-36.

8. The method of claim 1, wherein measuring the concentration, of the glycated peptide, or glycated fragment or glycated variant thereof, comprises contacting a sample from the host with an antibody, or conjugate comprising an antibody, that specifically binds to the glycated peptide or the glycated fragment or glycated variant thereof.

9. The method of claim 1, wherein measuring the concentration of the glycated peptide, or glycated fragment or glycated-variant thereof, comprises contacting a sample from the host with an aptamer, or conjugate comprising an aptamer, that specifically binds to the glycated peptide, or the glycated fragment or glycated variant thereof.

10. The method of claim 1, wherein the concentration of the glycated peptide, or glycated fragment or variant thereof, is measured in a sample of blood, blood plasma, or blood serum from the host.

11. The method of claim 1, further comprising measuring glycated hemoglobin A1C in the host.

12. The method of claim 1, further comprising measuring a blood glucose level of the host.

13. The method of claim 1, wherein the method is used to prevent a complication of diabetes, detect the onset, progression, or regression of diabetes, or determine the efficacy of a diabetes treatment.

14. The method of claim 1, wherein the method is used to detect diabetes or a predisposition to diabetes in the host, the method further comprising detecting an elevated concentration of the glycated peptide, or glycated fragment or glycated variant thereof, as compared to a control, wherein an elevation in the concentration of the glycated peptide, fragment, or variant as compared to a control is indicative of diabetes or a predisposition of diabetes in the host.

* * * * *

SEQUENCE LISTING

<160> NUMBER OF SEQ ID NOS: 47

<210> SEQ ID NO 1
<211> LENGTH: 10

```
<212> TYPE: PRT
<213> ORGANISM: Artificial
<220> FEATURE:
<223> OTHER INFORMATION: Synthetic

<400> SEQUENCE: 1

Ser Lys Glu Gln Leu Thr Pro Leu Ile Lys
1               5                   10

<210> SEQ ID NO 2
<211> LENGTH: 10
<212> TYPE: PRT
<213> ORGANISM: Artificial
<220> FEATURE:
<223> OTHER INFORMATION: Synthetic

<400> SEQUENCE: 2

Ser Ile Tyr Lys Pro Gly Gln Thr Val Lys
1               5                   10

<210> SEQ ID NO 3
<211> LENGTH: 11
<212> TYPE: PRT
<213> ORGANISM: Artificial
<220> FEATURE:
<223> OTHER INFORMATION: Synthetic

<400> SEQUENCE: 3

Val Lys Ser Pro Glu Leu Gln Ala Glu Ala Lys
1               5                   10

<210> SEQ ID NO 4
<211> LENGTH: 12
<212> TYPE: PRT
<213> ORGANISM: Artificial
<220> FEATURE:
<223> OTHER INFORMATION: Synthetic

<400> SEQUENCE: 4

Leu Val Asp Gly Lys Gly Val Pro Ile Pro Asn Lys
1               5                   10

<210> SEQ ID NO 5
<211> LENGTH: 13
<212> TYPE: PRT
<213> ORGANISM: Artificial
<220> FEATURE:
<223> OTHER INFORMATION: Synthetic

<400> SEQUENCE: 5

Ser Lys Ala Ile Gly Tyr Leu Asn Thr Gly Tyr Gln Arg
1               5                   10

<210> SEQ ID NO 6
<211> LENGTH: 9
<212> TYPE: PRT
<213> ORGANISM: Artificial
<220> FEATURE:
<223> OTHER INFORMATION: Synthetic

<400> SEQUENCE: 6

Gln Lys Leu His Glu Leu Gln Glu Lys
1               5

<210> SEQ ID NO 7
<211> LENGTH: 8
<212> TYPE: PRT
<213> ORGANISM: Artificial
```

```
<220> FEATURE:
<223> OTHER INFORMATION: Synthetic

<400> SEQUENCE: 7

Gly Lys Ile Thr Asp Leu Ile Lys
1               5

<210> SEQ ID NO 8
<211> LENGTH: 11
<212> TYPE: PRT
<213> ORGANISM: Artificial
<220> FEATURE:
<223> OTHER INFORMATION: Synthetic

<400> SEQUENCE: 8

Leu Glu Ala Leu Lys Glu Asn Gly Gly Ala Arg
1               5                   10

<210> SEQ ID NO 9
<211> LENGTH: 11
<212> TYPE: PRT
<213> ORGANISM: Artificial
<220> FEATURE:
<223> OTHER INFORMATION: Synthetic

<400> SEQUENCE: 9

Val Gln Pro Tyr Leu Asp Asp Phe Gln Lys Lys
1               5                   10

<210> SEQ ID NO 10
<211> LENGTH: 12
<212> TYPE: PRT
<213> ORGANISM: Artificial
<220> FEATURE:
<223> OTHER INFORMATION: Synthetic

<400> SEQUENCE: 10

Gly Asp Lys Val Trp Val Tyr Pro Pro Glu Lys Lys
1               5                   10

<210> SEQ ID NO 11
<211> LENGTH: 16
<212> TYPE: PRT
<213> ORGANISM: Artificial
<220> FEATURE:
<223> OTHER INFORMATION: Synthetic

<400> SEQUENCE: 11

Val Lys Ala His Tyr Gly Gly Phe Thr Val Gln Asn Glu Ala Asn Lys
1               5                   10                  15

<210> SEQ ID NO 12
<211> LENGTH: 11
<212> TYPE: PRT
<213> ORGANISM: Artificial
<220> FEATURE:
<223> OTHER INFORMATION: Synthetic

<400> SEQUENCE: 12

Gly Asp Lys Val Trp Val Tyr Pro Pro Glu Lys
1               5                   10

<210> SEQ ID NO 13
<211> LENGTH: 7
<212> TYPE: PRT
<213> ORGANISM: Artificial
<220> FEATURE:
<223> OTHER INFORMATION: Synthetic
```

```
<400> SEQUENCE: 13

Ser Tyr Phe Glu Lys Ser Lys
1               5

<210> SEQ ID NO 14
<211> LENGTH: 9
<212> TYPE: PRT
<213> ORGANISM: Artificial
<220> FEATURE:
<223> OTHER INFORMATION: Synthetic

<400> SEQUENCE: 14

Val Trp Val Tyr Pro Pro Glu Lys Lys
1               5

<210> SEQ ID NO 15
<211> LENGTH: 15
<212> TYPE: PRT
<213> ORGANISM: Artificial
<220> FEATURE:
<223> OTHER INFORMATION: Synthetic

<400> SEQUENCE: 15

Ala Gly Val Glu Thr Thr Thr Pro Ser Lys Gln Ser Asn Asn Lys
1               5                   10                  15

<210> SEQ ID NO 16
<211> LENGTH: 10
<212> TYPE: PRT
<213> ORGANISM: Artificial
<220> FEATURE:
<223> OTHER INFORMATION: Synthetic

<400> SEQUENCE: 16

Gly Phe Ser Pro Lys Asp Val Leu Val Arg
1               5                   10

<210> SEQ ID NO 17
<211> LENGTH: 9
<212> TYPE: PRT
<213> ORGANISM: Artificial
<220> FEATURE:
<223> OTHER INFORMATION: Synthetic

<400> SEQUENCE: 17

Leu Lys Phe Ile Ile Pro Ser Pro Lys
1               5

<210> SEQ ID NO 18
<211> LENGTH: 9
<212> TYPE: PRT
<213> ORGANISM: Artificial
<220> FEATURE:
<223> OTHER INFORMATION: Synthetic

<400> SEQUENCE: 18

Lys Ala Ser Tyr Leu Asp Cys Ile Arg
1               5

<210> SEQ ID NO 19
<211> LENGTH: 18
<212> TYPE: PRT
<213> ORGANISM: Artificial
<220> FEATURE:
<223> OTHER INFORMATION: Synthetic

<400> SEQUENCE: 19
```

Gly Asp Val Ala Phe Val Lys His Gln Thr Val Pro Gln Asn Thr Gly
1               5                   10                  15

Gly Lys

<210> SEQ ID NO 20
<211> LENGTH: 12
<212> TYPE: PRT
<213> ORGANISM: Artificial
<220> FEATURE:
<223> OTHER INFORMATION: Synthetic

<400> SEQUENCE: 20

Val Ser Asn Lys Ala Leu Pro Ala Pro Ile Glu Lys
1               5                   10

<210> SEQ ID NO 21
<211> LENGTH: 8
<212> TYPE: PRT
<213> ORGANISM: Artificial
<220> FEATURE:
<223> OTHER INFORMATION: Synthetic

<400> SEQUENCE: 21

Lys Gln Leu Val Glu Ile Glu Lys
1               5

<210> SEQ ID NO 22
<211> LENGTH: 12
<212> TYPE: PRT
<213> ORGANISM: Artificial
<220> FEATURE:
<223> OTHER INFORMATION: Synthetic

<400> SEQUENCE: 22

Ala Lys Val Gln Pro Tyr Leu Asp Asp Phe Gln Lys
1               5                   10

<210> SEQ ID NO 23
<211> LENGTH: 17
<212> TYPE: PRT
<213> ORGANISM: Artificial
<220> FEATURE:
<223> OTHER INFORMATION: Synthetic

<400> SEQUENCE: 23

Val Lys Ala His Tyr Gly Gly Phe Thr Val Gln Asn Glu Ala Asn Gln
1               5                   10                  15

Lys

<210> SEQ ID NO 24
<211> LENGTH: 77
<212> TYPE: PRT
<213> ORGANISM: Homo sapiens
<220> FEATURE:
<221> NAME/KEY: MISC_FEATURE
<223> OTHER INFORMATION: APO-A11 Region 24-100 of preprotein Acc. No.
      NP_001634.1

<400> SEQUENCE: 24

Gln Ala Lys Glu Pro Cys Val Glu Ser Leu Val Ser Gln Tyr Phe Gln
1               5                   10                  15

Thr Val Thr Asp Tyr Gly Lys Asp Leu Met Glu Lys Val Lys Ser Pro
                20                  25                  30

Glu Leu Gln Ala Glu Ala Lys Ser Tyr Phe Glu Lys Ser Lys Glu Gln
            35                  40                  45

```
Leu Thr Pro Leu Ile Lys Lys Ala Gly Thr Glu Leu Val Asn Phe Leu
    50                  55                  60

Ser Tyr Phe Val Glu Leu Gly Thr Gln Pro Ala Thr Gln
 65                  70                  75
```

```
<210> SEQ ID NO 25
<211> LENGTH: 1451
<212> TYPE: PRT
<213> ORGANISM: Homo sapiens
<220> FEATURE:
<221> NAME/KEY: MISC_FEATURE
<223> OTHER INFORMATION: Alpha-2M Region 24-1474 of preprotein Acc. No.
      NP_000005.2

<400> SEQUENCE: 25

Ser Val Ser Gly Lys Pro Gln Tyr Met Val Leu Val Pro Ser Leu Leu
 1               5                  10                  15

His Thr Glu Thr Thr Glu Lys Gly Cys Val Leu Leu Ser Tyr Leu Asn
                20                  25                  30

Glu Thr Val Thr Val Ser Ala Ser Leu Glu Ser Val Arg Gly Asn Arg
            35                  40                  45

Ser Leu Phe Thr Asp Leu Glu Ala Glu Asn Asp Val Leu His Cys Val
 50                  55                  60

Ala Phe Ala Val Pro Lys Ser Ser Asn Glu Glu Val Met Phe Leu
 65                  70                  75                  80

Thr Val Gln Val Lys Gly Pro Thr Gln Glu Phe Lys Lys Arg Thr Thr
                85                  90                  95

Val Met Val Lys Asn Glu Asp Ser Leu Val Phe Val Gln Thr Asp Lys
            100                 105                 110

Ser Ile Tyr Lys Pro Gly Gln Thr Val Lys Phe Arg Val Val Ser Met
        115                 120                 125

Asp Glu Asn Phe His Pro Leu Asn Glu Leu Ile Pro Leu Val Tyr Ile
130                 135                 140

Gln Asp Pro Lys Gly Asn Arg Ile Ala Gln Trp Gln Ser Phe Gln Leu
145                 150                 155                 160

Glu Gly Gly Leu Lys Gln Phe Ser Phe Pro Leu Ser Ser Glu Pro Phe
                165                 170                 175

Gln Gly Ser Tyr Lys Val Val Val Gln Lys Lys Ser Gly Gly Arg Thr
            180                 185                 190

Glu His Pro Phe Thr Val Glu Glu Phe Val Leu Pro Lys Phe Glu Val
        195                 200                 205

Gln Val Thr Val Pro Lys Ile Ile Thr Ile Leu Glu Glu Glu Met Asn
210                 215                 220

Val Ser Val Cys Gly Leu Tyr Thr Tyr Gly Lys Pro Val Pro Gly His
225                 230                 235                 240

Val Thr Val Ser Ile Cys Arg Lys Tyr Ser Asp Ala Ser Asp Cys His
                245                 250                 255

Gly Glu Asp Ser Gln Ala Phe Cys Glu Lys Phe Ser Gly Gln Leu Asn
            260                 265                 270

Ser His Gly Cys Phe Tyr Gln Gln Val Lys Thr Lys Val Phe Gln Leu
        275                 280                 285

Lys Arg Lys Glu Tyr Glu Met Lys Leu His Thr Glu Ala Gln Ile Gln
290                 295                 300

Glu Glu Gly Thr Val Val Glu Leu Thr Gly Arg Gln Ser Ser Glu Ile
305                 310                 315                 320

Thr Arg Thr Ile Thr Lys Leu Ser Phe Val Lys Val Asp Ser His Phe
```

-continued

```
                    325                 330                 335
Arg Gln Gly Ile Pro Phe Phe Gly Gln Val Arg Leu Val Asp Gly Lys
                340                 345                 350
Gly Val Pro Ile Pro Asn Lys Val Ile Phe Ile Arg Gly Asn Glu Ala
            355                 360                 365
Asn Tyr Tyr Ser Asn Ala Thr Thr Asp Glu His Gly Leu Val Gln Phe
370                 375                 380
Ser Ile Asn Thr Thr Asn Val Met Gly Thr Ser Leu Thr Val Arg Val
385                 390                 395                 400
Asn Tyr Lys Asp Arg Ser Pro Cys Tyr Gly Tyr Gln Trp Val Ser Glu
                405                 410                 415
Glu His Glu Glu Ala His His Thr Ala Tyr Leu Val Phe Ser Pro Ser
            420                 425                 430
Lys Ser Phe Val His Leu Glu Pro Met Ser His Glu Leu Pro Cys Gly
            435                 440                 445
His Thr Gln Thr Val Gln Ala His Tyr Ile Leu Asn Gly Gly Thr Leu
        450                 455                 460
Leu Gly Leu Lys Lys Leu Ser Phe Tyr Tyr Leu Ile Met Ala Lys Gly
465                 470                 475                 480
Gly Ile Val Arg Thr Gly Thr His Gly Leu Leu Val Lys Gln Glu Asp
                485                 490                 495
Met Lys Gly His Phe Ser Ile Ser Ile Pro Val Lys Ser Asp Ile Ala
                500                 505                 510
Pro Val Ala Arg Leu Leu Ile Tyr Ala Val Leu Pro Thr Gly Asp Val
            515                 520                 525
Ile Gly Asp Ser Ala Lys Tyr Asp Val Glu Asn Cys Leu Ala Asn Lys
530                 535                 540
Val Asp Leu Ser Phe Ser Pro Ser Gln Ser Leu Pro Ala Ser His Ala
545                 550                 555                 560
His Leu Arg Val Thr Ala Ala Pro Gln Ser Val Cys Ala Leu Arg Ala
                565                 570                 575
Val Asp Gln Ser Val Leu Leu Met Lys Pro Asp Ala Glu Leu Ser Ala
            580                 585                 590
Ser Ser Val Tyr Asn Leu Leu Pro Glu Lys Asp Leu Thr Gly Phe Pro
        595                 600                 605
Gly Pro Leu Asn Asp Gln Asp Asp Glu Asp Cys Ile Asn Arg His Asn
            610                 615                 620
Val Tyr Ile Asn Gly Ile Thr Tyr Thr Pro Val Ser Ser Thr Asn Glu
625                 630                 635                 640
Lys Asp Met Tyr Ser Phe Leu Glu Asp Met Gly Leu Lys Ala Phe Thr
                645                 650                 655
Asn Ser Lys Ile Arg Lys Pro Lys Met Cys Pro Gln Leu Gln Gln Tyr
            660                 665                 670
Glu Met His Gly Pro Glu Gly Leu Arg Val Gly Phe Tyr Glu Ser Asp
            675                 680                 685
Val Met Gly Arg Gly His Ala Arg Leu Val His Val Glu Glu Pro His
        690                 695                 700
Thr Glu Thr Val Arg Lys Tyr Phe Pro Glu Thr Trp Ile Trp Asp Leu
705                 710                 715                 720
Val Val Val Asn Ser Ala Gly Val Ala Glu Val Gly Val Thr Val Pro
                725                 730                 735
Asp Thr Ile Thr Glu Trp Lys Ala Gly Ala Phe Cys Leu Ser Glu Asp
            740                 745                 750
```

-continued

```
Ala Gly Leu Gly Ile Ser Ser Thr Ala Ser Leu Arg Ala Phe Gln Pro
            755                 760                 765

Phe Phe Val Glu Leu Thr Met Pro Tyr Ser Val Ile Arg Gly Glu Ala
770                 775                 780

Phe Thr Leu Lys Ala Thr Val Leu Asn Tyr Leu Pro Lys Cys Ile Arg
785                 790                 795                 800

Val Ser Val Gln Leu Glu Ala Ser Pro Ala Phe Leu Ala Val Pro Val
            805                 810                 815

Glu Lys Glu Gln Ala Pro His Cys Ile Cys Ala Asn Gly Arg Gln Thr
            820                 825                 830

Val Ser Trp Ala Val Thr Pro Lys Ser Leu Gly Asn Val Asn Phe Thr
            835                 840                 845

Val Ser Ala Glu Ala Leu Glu Ser Gln Glu Leu Cys Gly Thr Glu Val
            850                 855                 860

Pro Ser Val Pro Glu His Gly Arg Lys Asp Thr Val Ile Lys Pro Leu
865                 870                 875                 880

Leu Val Glu Pro Glu Gly Leu Glu Lys Glu Thr Thr Phe Asn Ser Leu
                885                 890                 895

Leu Cys Pro Ser Gly Gly Glu Val Ser Glu Glu Leu Ser Leu Lys Leu
            900                 905                 910

Pro Pro Asn Val Val Glu Glu Ser Ala Arg Ala Ser Val Ser Val Leu
            915                 920                 925

Gly Asp Ile Leu Gly Ser Ala Met Gln Asn Thr Gln Asn Leu Leu Gln
            930                 935                 940

Met Pro Tyr Gly Cys Gly Glu Gln Asn Met Val Leu Phe Ala Pro Asn
945                 950                 955                 960

Ile Tyr Val Leu Asp Tyr Leu Asn Glu Thr Gln Gln Leu Thr Pro Glu
                965                 970                 975

Ile Lys Ser Lys Ala Ile Gly Tyr Leu Asn Thr Gly Tyr Gln Arg Gln
            980                 985                 990

Leu Asn Tyr Lys His Tyr Asp Gly Ser Tyr Ser Thr Phe Gly Glu Arg
            995                 1000                1005

Tyr Gly Arg Asn Gln Gly Asn Thr Trp Leu Thr Ala Phe Val Leu
    1010                1015                1020

Lys Thr Phe Ala Gln Ala Arg Ala Tyr Ile Phe Ile Asp Glu Ala
    1025                1030                1035

His Ile Thr Gln Ala Leu Ile Trp Leu Ser Gln Arg Gln Lys Asp
    1040                1045                1050

Asn Gly Cys Phe Arg Ser Ser Gly Ser Leu Leu Asn Asn Ala Ile
    1055                1060                1065

Lys Gly Gly Val Glu Asp Glu Val Thr Leu Ser Ala Tyr Ile Thr
    1070                1075                1080

Ile Ala Leu Leu Glu Ile Pro Leu Thr Val Thr His Pro Val Val
    1085                1090                1095

Arg Asn Ala Leu Phe Cys Leu Glu Ser Ala Trp Lys Thr Ala Gln
    1100                1105                1110

Glu Gly Asp His Gly Ser His Val Tyr Thr Lys Ala Leu Leu Ala
    1115                1120                1125

Tyr Ala Phe Ala Leu Ala Gly Asn Gln Asp Lys Arg Lys Glu Val
    1130                1135                1140

Leu Lys Ser Leu Asn Glu Glu Ala Val Lys Lys Asp Asn Ser Val
    1145                1150                1155

His Trp Glu Arg Pro Gln Lys Pro Lys Ala Pro Val Gly His Phe
    1160                1165                1170
```

```
Tyr Glu Pro Gln Ala Pro Ser Ala Glu Val Glu Met Thr Ser Tyr
    1175            1180            1185

Val Leu Leu Ala Tyr Leu Thr Ala Gln Pro Ala Pro Thr Ser Glu
    1190            1195            1200

Asp Leu Thr Ser Ala Thr Asn Ile Val Lys Trp Ile Thr Lys Gln
    1205            1210            1215

Gln Asn Ala Gln Gly Gly Phe Ser Ser Thr Gln Asp Thr Val Val
    1220            1225            1230

Ala Leu His Ala Leu Ser Lys Tyr Gly Ala Ala Thr Phe Thr Arg
    1235            1240            1245

Thr Gly Lys Ala Ala Gln Val Thr Ile Gln Ser Ser Gly Thr Phe
    1250            1255            1260

Ser Ser Lys Phe Gln Val Asp Asn Asn Asn Arg Leu Leu Leu Gln
    1265            1270            1275

Gln Val Ser Leu Pro Glu Leu Pro Gly Glu Tyr Ser Met Lys Val
    1280            1285            1290

Thr Gly Glu Gly Cys Val Tyr Leu Gln Thr Ser Leu Lys Tyr Asn
    1295            1300            1305

Ile Leu Pro Glu Lys Glu Glu Phe Pro Phe Ala Leu Gly Val Gln
    1310            1315            1320

Thr Leu Pro Gln Thr Cys Asp Glu Pro Lys Ala His Thr Ser Phe
    1325            1330            1335

Gln Ile Ser Leu Ser Val Ser Tyr Thr Gly Ser Arg Ser Ala Ser
    1340            1345            1350

Asn Met Ala Ile Val Asp Val Lys Met Val Ser Gly Phe Ile Pro
    1355            1360            1365

Leu Lys Pro Thr Val Lys Met Leu Glu Arg Ser Asn His Val Ser
    1370            1375            1380

Arg Thr Glu Val Ser Ser Asn His Val Leu Ile Tyr Leu Asp Lys
    1385            1390            1395

Val Ser Asn Gln Thr Leu Ser Leu Phe Phe Thr Val Leu Gln Asp
    1400            1405            1410

Val Pro Val Arg Asp Leu Lys Pro Ala Ile Val Lys Val Tyr Asp
    1415            1420            1425

Tyr Tyr Glu Thr Asp Glu Phe Ala Ile Ala Glu Tyr Asn Ala Pro
    1430            1435            1440

Cys Ser Lys Asp Leu Gly Asn Ala
    1445            1450

<210> SEQ ID NO 26
<211> LENGTH: 243
<212> TYPE: PRT
<213> ORGANISM: Homo sapiens
<220> FEATURE:
<221> NAME/KEY: MISC_FEATURE
<223> OTHER INFORMATION: APO-A1 Region 25-267 of preprotein NP_000030.1

<400> SEQUENCE: 26

Asp Glu Pro Pro Gln Ser Pro Trp Asp Arg Val Lys Asp Leu Ala Thr
1               5                   10                  15

Val Tyr Val Asp Val Leu Lys Asp Ser Gly Arg Asp Tyr Val Ser Gln
            20                  25                  30

Phe Glu Gly Ser Ala Leu Gly Lys Gln Leu Asn Leu Lys Leu Leu Asp
        35                  40                  45

Asn Trp Asp Ser Val Thr Ser Thr Phe Ser Lys Leu Arg Glu Gln Leu
    50                  55                  60
```

```
Gly Pro Val Thr Gln Glu Phe Trp Asp Asn Leu Glu Lys Glu Thr Glu
 65                  70                  75                  80

Gly Leu Arg Gln Glu Met Ser Lys Asp Leu Glu Glu Val Lys Ala Lys
             85                  90                  95

Val Gln Pro Tyr Leu Asp Asp Phe Gln Lys Lys Trp Gln Glu Glu Met
            100                 105                 110

Glu Leu Tyr Arg Gln Lys Val Glu Pro Leu Arg Ala Glu Leu Gln Glu
            115                 120                 125

Gly Ala Arg Gln Lys Leu His Glu Leu Gln Glu Lys Leu Ser Pro Leu
130                 135                 140

Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Arg Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
            195                 200                 205

Pro Ala Leu Glu Asp Leu Arg Gln Gly Leu Leu Pro Val Leu Glu Ser
210                 215                 220

Phe Lys Val Ser Phe Leu Ser Ala Leu Glu Glu Tyr Thr Lys Lys Leu
225                 230                 235                 240

Asn Thr Gln

<210> SEQ ID NO 27
<211> LENGTH: 398
<212> TYPE: PRT
<213> ORGANISM: Homo sapiens
<220> FEATURE:
<221> NAME/KEY: MISC_FEATURE
<223> OTHER INFORMATION: Serpin Peptidase Inhibitor Region 26-423 of
      preprotein Acc. No. NP_001076.2

<400> SEQUENCE: 27

Asn Ser Pro Leu Asp Glu Glu Asn Leu Thr Gln Glu Asn Gln Asp Arg
 1               5                  10                  15

Gly Thr His Val Asp Leu Gly Leu Ala Ser Ala Asn Val Asp Phe Ala
             20                  25                  30

Phe Ser Leu Tyr Lys Gln Leu Val Leu Lys Ala Pro Asp Lys Asn Val
             35                  40                  45

Ile Phe Ser Pro Leu Ser Ile Ser Thr Ala Leu Ala Phe Leu Ser Leu
 50                  55                  60

Gly Ala His Asn Thr Thr Leu Thr Glu Ile Leu Lys Gly Leu Lys Phe
 65                  70                  75                  80

Asn Leu Thr Glu Thr Ser Glu Ala Glu Ile His Gln Ser Phe Gln His
             85                  90                  95

Leu Leu Arg Thr Leu Asn Gln Ser Ser Asp Glu Leu Gln Leu Ser Met
            100                 105                 110

Gly Asn Ala Met Phe Val Lys Glu Gln Leu Ser Leu Leu Asp Arg Phe
            115                 120                 125

Thr Glu Asp Ala Lys Arg Leu Tyr Gly Ser Glu Ala Phe Ala Thr Asp
130                 135                 140

Phe Gln Asp Ser Ala Ala Ala Lys Lys Leu Ile Asn Asp Tyr Val Lys
145                 150                 155                 160

Asn Gly Thr Arg Gly Lys Ile Thr Asp Leu Ile Lys Asp Leu Asp Ser
                165                 170                 175
```

Gln Thr Met Met Val Leu Val Asn Tyr Ile Phe Phe Lys Ala Lys Trp
            180                 185                 190

Glu Met Pro Phe Asp Pro Gln Asp Thr His Gln Ser Arg Phe Tyr Leu
            195                 200                 205

Ser Lys Lys Lys Trp Val Met Val Pro Met Met Ser Leu His His Leu
210                 215                 220

Thr Ile Pro Tyr Phe Arg Asp Glu Glu Leu Ser Cys Thr Val Val Glu
225                 230                 235                 240

Leu Lys Tyr Thr Gly Asn Ala Ser Ala Leu Phe Ile Leu Pro Asp Gln
            245                 250                 255

Asp Lys Met Glu Glu Val Glu Ala Met Leu Leu Pro Glu Thr Leu Lys
            260                 265                 270

Arg Trp Arg Asp Ser Leu Glu Phe Arg Glu Ile Gly Glu Leu Tyr Leu
            275                 280                 285

Pro Lys Phe Ser Ile Ser Arg Asp Tyr Asn Leu Asn Asp Ile Leu Leu
            290                 295                 300

Gln Leu Gly Ile Glu Glu Ala Phe Thr Ser Lys Ala Asp Leu Ser Gly
305                 310                 315                 320

Ile Thr Gly Ala Arg Asn Leu Ala Val Ser Gln Val Val His Lys Ala
            325                 330                 335

Val Leu Asp Val Phe Glu Glu Gly Thr Glu Ala Ser Ala Ala Thr Ala
            340                 345                 350

Val Lys Ile Thr Leu Leu Ser Ala Leu Val Glu Thr Arg Thr Ile Val
            355                 360                 365

Arg Phe Asn Arg Pro Phe Leu Met Ile Ile Val Pro Thr Asp Thr Gln
            370                 375                 380

Asn Ile Phe Phe Met Ser Lys Val Thr Asn Pro Lys Gln Ala
385                 390                 395

<210> SEQ ID NO 28
<211> LENGTH: 439
<212> TYPE: PRT
<213> ORGANISM: Homo sapiens
<220> FEATURE:
<221> NAME/KEY: MISC_FEATURE
<223> OTHER INFORMATION: Hemopexin Region 24-462 of preprotein Acc. no.
      NP_000604.1

<400> SEQUENCE: 28

Thr Pro Leu Pro Pro Thr Ser Ala His Gly Asn Val Ala Glu Gly Glu
1               5                   10                  15

Thr Lys Pro Asp Pro Asp Val Thr Glu Arg Cys Ser Asp Gly Trp Ser
            20                  25                  30

Phe Asp Ala Thr Thr Leu Asp Asp Asn Gly Thr Met Leu Phe Phe Lys
            35                  40                  45

Gly Glu Phe Val Trp Lys Ser His Lys Trp Asp Arg Glu Leu Ile Ser
        50                  55                  60

Glu Arg Trp Lys Asn Phe Pro Ser Pro Val Asp Ala Ala Phe Arg Gln
65                  70                  75                  80

Gly His Asn Ser Val Phe Leu Ile Lys Gly Asp Lys Val Trp Val Tyr
            85                  90                  95

Pro Pro Glu Lys Lys Glu Lys Gly Tyr Pro Lys Leu Leu Gln Asp Glu
            100                 105                 110

Phe Pro Gly Ile Pro Ser Pro Leu Asp Ala Ala Val Glu Cys His Arg
            115                 120                 125

Gly Glu Cys Gln Ala Glu Gly Val Leu Phe Phe Gln Gly Asp Arg Glu

-continued

```
            130                 135                 140
Trp Phe Trp Asp Leu Ala Thr Gly Thr Met Lys Glu Arg Ser Trp Pro
145                 150                 155                 160

Ala Val Gly Asn Cys Ser Ser Ala Leu Arg Trp Leu Gly Arg Tyr Tyr
                165                 170                 175

Cys Phe Gln Gly Asn Gln Phe Leu Arg Phe Asp Pro Val Arg Gly Glu
            180                 185                 190

Val Pro Pro Arg Tyr Pro Arg Asp Val Arg Asp Tyr Phe Met Pro Cys
                195                 200                 205

Pro Gly Arg Gly His Gly His Arg Asn Gly Thr Gly His Gly Asn Ser
210                 215                 220

Thr His His Gly Pro Glu Tyr Met Arg Cys Ser Pro His Leu Val Leu
225                 230                 235                 240

Ser Ala Leu Thr Ser Asp Asn His Gly Ala Thr Tyr Ala Phe Ser Gly
                245                 250                 255

Thr His Tyr Trp Arg Leu Asp Thr Ser Arg Asp Gly Trp His Ser Trp
            260                 265                 270

Pro Ile Ala His Gln Trp Pro Gln Gly Pro Ser Ala Val Asp Ala Ala
            275                 280                 285

Phe Ser Trp Glu Glu Lys Leu Tyr Leu Val Gln Gly Thr Gln Val Tyr
290                 295                 300

Val Phe Leu Thr Lys Gly Gly Tyr Thr Leu Val Ser Gly Tyr Pro Lys
305                 310                 315                 320

Arg Leu Glu Lys Glu Val Gly Thr Pro His Gly Ile Ile Leu Asp Ser
                325                 330                 335

Val Asp Ala Ala Phe Ile Cys Pro Gly Ser Ser Arg Leu His Ile Met
                340                 345                 350

Ala Gly Arg Arg Leu Trp Trp Leu Asp Leu Lys Ser Gly Ala Gln Ala
            355                 360                 365

Thr Trp Thr Glu Leu Pro Trp Pro His Glu Lys Val Asp Gly Ala Leu
            370                 375                 380

Cys Met Glu Lys Ser Leu Gly Pro Asn Ser Cys Ser Ala Asn Gly Pro
385                 390                 395                 400

Gly Leu Tyr Leu Ile His Gly Pro Asn Leu Tyr Cys Tyr Ser Asp Val
                405                 410                 415

Glu Lys Leu Asn Ala Ala Lys Ala Leu Pro Gln Pro Gln Asn Val Thr
            420                 425                 430

Ser Leu Leu Gly Cys Thr His
            435
```

```
<210> SEQ ID NO 29
<211> LENGTH: 491
<212> TYPE: PRT
<213> ORGANISM: Homo sapiens
<220> FEATURE:
<221> NAME/KEY: MISC_FEATURE
<223> OTHER INFORMATION: Fibrinogen Beta Chain Region 45-491 of
      preprotein Acc. No. NP_005132.2

<400> SEQUENCE: 29

Met Lys Arg Met Val Ser Trp Ser Phe His Lys Leu Lys Thr Met Lys
1               5                   10                  15

His Leu Leu Leu Leu Leu Leu Cys Val Phe Leu Val Lys Ser Gln Gly
                20                  25                  30

Val Asn Asp Asn Glu Glu Gly Phe Phe Ser Ala Arg Gly His Arg Pro
            35                  40                  45
```

```
Leu Asp Lys Lys Arg Glu Glu Ala Pro Ser Leu Arg Pro Ala Pro Pro
     50                  55                  60

Pro Ile Ser Gly Gly Tyr Arg Ala Arg Pro Ala Lys Ala Ala Ala
 65              70                  75                  80

Thr Gln Lys Lys Val Glu Arg Lys Ala Pro Asp Ala Gly Gly Cys Leu
                     85                  90                  95

His Ala Asp Pro Asp Leu Gly Val Leu Cys Pro Thr Gly Cys Gln Leu
             100                 105                 110

Gln Glu Ala Leu Leu Gln Glu Arg Pro Ile Arg Asn Ser Val Asp
         115                 120                 125

Glu Leu Asn Asn Asn Val Glu Ala Val Ser Gln Thr Ser Ser Ser
 130                 135                 140

Phe Gln Tyr Met Tyr Leu Leu Lys Asp Leu Trp Gln Lys Arg Gln Lys
145                 150                 155                 160

Gln Val Lys Asp Asn Glu Asn Val Val Asn Glu Tyr Ser Ser Glu Leu
                 165                 170                 175

Glu Lys His Gln Leu Tyr Ile Asp Glu Thr Val Asn Ser Asn Ile Pro
             180                 185                 190

Thr Asn Leu Arg Val Leu Arg Ser Ile Leu Glu Asn Leu Arg Ser Lys
         195                 200                 205

Ile Gln Lys Leu Glu Ser Asp Val Ser Ala Gln Met Glu Tyr Cys Arg
210                 215                 220

Thr Pro Cys Thr Val Ser Cys Asn Ile Pro Val Val Ser Gly Lys Glu
225                 230                 235                 240

Cys Glu Glu Ile Ile Arg Lys Gly Gly Glu Thr Ser Glu Met Tyr Leu
                 245                 250                 255

Ile Gln Pro Asp Ser Ser Val Lys Pro Tyr Arg Val Tyr Cys Asp Met
             260                 265                 270

Asn Thr Glu Asn Gly Gly Trp Thr Val Ile Gln Asn Arg Gln Asp Gly
         275                 280                 285

Ser Val Asp Phe Gly Arg Lys Trp Asp Pro Tyr Lys Gln Gly Phe Gly
     290                 295                 300

Asn Val Ala Thr Asn Thr Asp Gly Lys Asn Tyr Cys Gly Leu Pro Gly
305                 310                 315                 320

Glu Tyr Trp Leu Gly Asn Asp Lys Ile Ser Gln Leu Thr Arg Met Gly
                 325                 330                 335

Pro Thr Glu Leu Leu Ile Glu Met Glu Asp Trp Lys Gly Asp Lys Val
             340                 345                 350

Lys Ala His Tyr Gly Gly Phe Thr Val Gln Asn Glu Ala Asn Lys Tyr
         355                 360                 365

Gln Ile Ser Val Asn Lys Tyr Arg Gly Thr Ala Gly Asn Ala Leu Met
     370                 375                 380

Asp Gly Ala Ser Gln Leu Met Gly Glu Asn Arg Thr Met Thr Ile His
385                 390                 395                 400

Asn Gly Met Phe Phe Ser Thr Tyr Asp Arg Asp Asn Asp Gly Trp Leu
                 405                 410                 415

Thr Ser Asp Pro Arg Lys Gln Cys Ser Lys Glu Asp Gly Gly Trp
             420                 425                 430

Trp Tyr Asn Arg Cys His Ala Ala Asn Pro Asn Gly Arg Tyr Tyr Trp
         435                 440                 445

Gly Gly Gln Tyr Thr Trp Asp Met Ala Lys His Gly Thr Asp Asp Gly
     450                 455                 460

Val Val Trp Met Asn Trp Lys Gly Ser Trp Tyr Ser Met Arg Lys Met
465                 470                 475                 480
```

```
Ser Met Lys Ile Arg Pro Phe Phe Pro Gln Gln
            485             490

<210> SEQ ID NO 30
<211> LENGTH: 104
<212> TYPE: PRT
<213> ORGANISM: Homo sapiens
<220> FEATURE:
<221> NAME/KEY: MISC_FEATURE
<223> OTHER INFORMATION: Ig lambda light chain Acc. No. AAA59109

<400> SEQUENCE: 30

Pro Lys Ala Ala Pro Ser Val Thr Leu Phe Pro Pro Ser Ser Glu Glu
1               5                   10                  15

Leu Gln Ala Asn Lys Ala Thr Leu Val Cys Leu Ile Ser Asp Phe Tyr
            20                  25                  30

Pro Gly Ala Val Thr Val Ala Trp Lys Ala Asp Ser Ser Pro Val Lys
        35                  40                  45

Ala Gly Val Glu Thr Thr Thr Pro Ser Lys Gln Ser Asn Asn Lys Tyr
    50                  55                  60

Ala Ala Ser Ser Tyr Leu Ser Leu Thr Pro Glu Gln Trp Lys Ser His
65                  70                  75                  80

Lys Ser Tyr Ser Cys Gln Val Thr His Glu Gly Ser Thr Val Glu Lys
                85                  90                  95

Thr Val Ala Pro Thr Glu Cys Ser
            100

<210> SEQ ID NO 31
<211> LENGTH: 220
<212> TYPE: PRT
<213> ORGANISM: Homo sapiens
<220> FEATURE:
<221> NAME/KEY: MISC_FEATURE
<223> OTHER INFORMATION: Ig heavy chain constant region Acc. No.
      CAA09968

<400> SEQUENCE: 31

Leu Glu Asp Leu Leu Leu Gly Ser Glu Ala Asn Leu Thr Cys Thr Leu
1               5                   10                  15

Thr Gly Leu Arg Asp Ala Ser Gly Ala Thr Phe Thr Trp Thr Pro Ser
            20                  25                  30

Ser Gly Lys Ser Ala Val Gln Gly Pro Pro Glu Arg Asp Leu Cys Gly
        35                  40                  45

Cys Tyr Ser Val Ser Ser Val Leu Pro Gly Cys Ala Gln Pro Trp Asn
    50                  55                  60

His Gly Glu Thr Phe Thr Cys Thr Ala Ala His Pro Glu Leu Lys Thr
65                  70                  75                  80

Pro Leu Thr Ala Asn Ile Thr Lys Ser Gly Asn Thr Phe Arg Pro Glu
                85                  90                  95

Val His Leu Leu Pro Pro Ser Glu Glu Leu Ala Leu Asn Glu Leu
            100                 105                 110

Val Thr Leu Thr Cys Leu Ala Arg Gly Phe Ser Pro Lys Asp Val Leu
        115                 120                 125

Val Arg Trp Leu Gln Gly Ser Gln Glu Leu Pro Arg Glu Lys Tyr Leu
    130                 135                 140

Thr Trp Ala Ser Arg Gln Glu Pro Ser Gln Gly Thr Thr Thr Tyr Ala
145                 150                 155                 160

Val Thr Ser Ile Leu Arg Val Ala Ala Glu Asp Trp Lys Lys Gly Glu
                165                 170                 175
```

```
Thr Phe Ser Cys Met Val Gly His Glu Ala Leu Pro Leu Ala Phe Thr
            180                 185                 190

Gln Lys Thr Ile Asp Arg Met Ala Gly Lys Pro Thr His Ile Asn Val
        195                 200                 205

Ser Val Val Met Ala Glu Ala Asp Gly Thr Cys Tyr
    210                 215                 220

<210> SEQ ID NO 32
<211> LENGTH: 4536
<212> TYPE: PRT
<213> ORGANISM: Homo sapiens
<220> FEATURE:
<221> NAME/KEY: MISC_FEATURE
<223> OTHER INFORMATION: APO B100 Region 28-4563 of preprotein Acc. No.
      NP_000375.1

<400> SEQUENCE: 32

Glu Glu Glu Met Leu Glu Asn Val Ser Leu Val Cys Pro Lys Asp Ala
1               5                   10                  15

Thr Arg Phe Lys His Leu Arg Lys Tyr Thr Tyr Asn Tyr Glu Ala Glu
            20                  25                  30

Ser Ser Ser Gly Val Pro Gly Thr Ala Asp Ser Arg Ser Ala Thr Arg
        35                  40                  45

Ile Asn Cys Lys Val Glu Leu Glu Val Pro Gln Leu Cys Ser Phe Ile
    50                  55                  60

Leu Lys Thr Ser Gln Cys Thr Leu Lys Glu Val Tyr Gly Phe Asn Pro
65                  70                  75                  80

Glu Gly Lys Ala Leu Leu Lys Lys Thr Lys Asn Ser Glu Glu Phe Ala
                85                  90                  95

Ala Ala Met Ser Arg Tyr Glu Leu Lys Leu Ala Ile Pro Glu Gly Lys
            100                 105                 110

Gln Val Phe Leu Tyr Pro Glu Lys Asp Glu Pro Thr Tyr Ile Leu Asn
        115                 120                 125

Ile Lys Arg Gly Ile Ile Ser Ala Leu Leu Val Pro Pro Glu Thr Glu
    130                 135                 140

Glu Ala Lys Gln Val Leu Phe Leu Asp Thr Val Tyr Gly Asn Cys Ser
145                 150                 155                 160

Thr His Phe Thr Val Lys Thr Arg Lys Gly Asn Val Ala Thr Glu Ile
                165                 170                 175

Ser Thr Glu Arg Asp Leu Gly Gln Cys Asp Arg Phe Lys Pro Ile Arg
            180                 185                 190

Thr Gly Ile Ser Pro Leu Ala Leu Ile Lys Gly Met Thr Arg Pro Leu
        195                 200                 205

Ser Thr Leu Ile Ser Ser Ser Gln Ser Cys Gln Tyr Thr Leu Asp Ala
    210                 215                 220

Lys Arg Lys His Val Ala Glu Ala Ile Cys Lys Glu Gln His Leu Phe
225                 230                 235                 240

Leu Pro Phe Ser Tyr Asn Asn Lys Tyr Gly Met Val Ala Gln Val Thr
                245                 250                 255

Gln Thr Leu Lys Leu Glu Asp Thr Pro Lys Ile Asn Ser Arg Phe Phe
            260                 265                 270

Gly Glu Gly Thr Lys Lys Met Gly Leu Ala Phe Glu Ser Thr Lys Ser
        275                 280                 285

Thr Ser Pro Pro Lys Gln Ala Glu Ala Val Leu Lys Thr Leu Gln Glu
    290                 295                 300

Leu Lys Lys Leu Thr Ile Ser Glu Gln Asn Ile Gln Arg Ala Asn Leu
```

```
            305                 310                 315                 320

Phe Asn Lys Leu Val Thr Glu Leu Arg Gly Leu Ser Asp Glu Ala Val
                325                 330                 335

Thr Ser Leu Leu Pro Gln Leu Ile Glu Val Ser Ser Pro Ile Thr Leu
                340                 345                 350

Gln Ala Leu Val Gln Cys Gly Gln Pro Gln Cys Ser Thr His Ile Leu
                355                 360                 365

Gln Trp Leu Lys Arg Val His Ala Asn Pro Leu Leu Ile Asp Val Val
                370                 375                 380

Thr Tyr Leu Val Ala Leu Ile Pro Glu Pro Ser Ala Gln Gln Leu Arg
385                 390                 395                 400

Glu Ile Phe Asn Met Ala Arg Asp Gln Arg Ser Arg Ala Thr Leu Tyr
                405                 410                 415

Ala Leu Ser His Ala Val Asn Asn Tyr His Lys Thr Asn Pro Thr Gly
                420                 425                 430

Thr Gln Glu Leu Leu Asp Ile Ala Asn Tyr Leu Met Glu Gln Ile Gln
                435                 440                 445

Asp Asp Cys Thr Gly Asp Glu Asp Tyr Thr Tyr Leu Ile Leu Arg Val
                450                 455                 460

Ile Gly Asn Met Gly Gln Thr Met Glu Gln Leu Thr Pro Glu Leu Lys
465                 470                 475                 480

Ser Ser Ile Leu Lys Cys Val Gln Ser Thr Lys Pro Ser Leu Met Ile
                485                 490                 495

Gln Lys Ala Ala Ile Gln Ala Leu Arg Lys Met Glu Pro Lys Asp Lys
                500                 505                 510

Asp Gln Glu Val Leu Leu Gln Thr Phe Leu Asp Asp Ala Ser Pro Gly
                515                 520                 525

Asp Lys Arg Leu Ala Ala Tyr Leu Met Leu Met Arg Ser Pro Ser Gln
                530                 535                 540

Ala Asp Ile Asn Lys Ile Val Gln Ile Leu Pro Trp Glu Gln Asn Glu
545                 550                 555                 560

Gln Val Lys Asn Phe Val Ala Ser His Ile Ala Asn Ile Leu Asn Ser
                565                 570                 575

Glu Glu Leu Asp Ile Gln Asp Leu Lys Lys Leu Val Lys Glu Ala Leu
                580                 585                 590

Lys Glu Ser Gln Leu Pro Thr Val Met Asp Phe Arg Lys Phe Ser Arg
                595                 600                 605

Asn Tyr Gln Leu Tyr Lys Ser Val Ser Leu Pro Ser Leu Asp Pro Ala
                610                 615                 620

Ser Ala Lys Ile Glu Gly Asn Leu Ile Phe Asp Pro Asn Asn Tyr Leu
625                 630                 635                 640

Pro Lys Glu Ser Met Leu Lys Thr Thr Leu Thr Ala Phe Gly Phe Ala
                645                 650                 655

Ser Ala Asp Leu Ile Glu Ile Gly Leu Glu Gly Lys Gly Phe Glu Pro
                660                 665                 670

Thr Leu Glu Ala Leu Phe Gly Lys Gln Gly Phe Phe Pro Asp Ser Val
                675                 680                 685

Asn Lys Ala Leu Tyr Trp Val Asn Gly Gln Val Pro Asp Gly Val Ser
                690                 695                 700

Lys Val Leu Val Asp His Phe Gly Tyr Thr Lys Asp Asp Lys His Glu
705                 710                 715                 720

Gln Asp Met Val Asn Gly Ile Met Leu Ser Val Glu Lys Leu Ile Lys
                725                 730                 735
```

```
Asp Leu Lys Ser Lys Glu Val Pro Glu Ala Arg Ala Tyr Leu Arg Ile
            740                 745                 750

Leu Gly Glu Glu Leu Gly Phe Ala Ser Leu His Asp Leu Gln Leu Leu
        755                 760                 765

Gly Lys Leu Leu Leu Met Gly Ala Arg Thr Leu Gln Gly Ile Pro Gln
    770                 775                 780

Met Ile Gly Glu Val Ile Arg Lys Gly Ser Lys Asn Asp Phe Phe Leu
785                 790                 795                 800

His Tyr Ile Phe Met Glu Asn Ala Phe Glu Leu Pro Thr Gly Ala Gly
                805                 810                 815

Leu Gln Leu Gln Ile Ser Ser Gly Val Ile Ala Pro Gly Ala Lys
            820                 825                 830

Ala Gly Val Lys Leu Glu Val Ala Asn Met Gln Ala Glu Leu Val Ala
        835                 840                 845

Lys Pro Ser Val Ser Val Glu Phe Val Thr Asn Met Gly Ile Ile Ile
    850                 855                 860

Pro Asp Phe Ala Arg Ser Gly Val Gln Met Asn Thr Asn Phe Phe His
865                 870                 875                 880

Glu Ser Gly Leu Glu Ala His Val Ala Leu Lys Ala Gly Lys Leu Lys
                885                 890                 895

Phe Ile Ile Pro Ser Pro Lys Arg Pro Val Lys Leu Leu Ser Gly Gly
            900                 905                 910

Asn Thr Leu His Leu Val Ser Thr Thr Lys Thr Glu Val Ile Pro Pro
        915                 920                 925

Leu Ile Glu Asn Arg Gln Ser Trp Ser Val Cys Lys Gln Val Phe Pro
    930                 935                 940

Gly Leu Asn Tyr Cys Thr Ser Gly Ala Tyr Ser Asn Ala Ser Ser Thr
945                 950                 955                 960

Asp Ser Ala Ser Tyr Tyr Pro Leu Thr Gly Asp Thr Arg Leu Glu Leu
                965                 970                 975

Glu Leu Arg Pro Thr Gly Glu Ile Glu Gln Tyr Ser Val Ser Ala Thr
            980                 985                 990

Tyr Glu Leu Gln Arg Glu Asp Arg  Ala Leu Val Asp Thr  Leu Lys Phe
        995                 1000                1005

Val Thr  Gln Ala Glu Gly Ala  Lys Gln Thr Glu Ala  Thr Met Thr
    1010                1015                1020

Phe Lys  Tyr Asn Arg Gln Ser  Met Thr Leu Ser Ser  Glu Val Gln
    1025                1030                1035

Ile Pro  Asp Phe Asp Val Asp  Leu Gly Thr Ile Leu  Arg Val Asn
    1040                1045                1050

Asp Glu  Ser Thr Glu Gly Lys  Thr Ser Tyr Arg Leu  Thr Leu Asp
    1055                1060                1065

Ile Gln  Asn Lys Lys Ile Thr  Glu Val Ala Leu Met  Gly His Leu
    1070                1075                1080

Ser Cys  Asp Thr Lys Glu Glu  Arg Lys Ile Lys Gly  Val Ile Ser
    1085                1090                1095

Ile Pro  Arg Leu Gln Ala Glu  Ala Arg Ser Glu Ile  Leu Ala His
    1100                1105                1110

Trp Ser  Pro Ala Lys Leu Leu  Leu Gln Met Asp Ser  Ser Ala Thr
    1115                1120                1125

Ala Tyr  Gly Ser Thr Val Ser  Lys Arg Val Ala Trp  His Tyr Asp
    1130                1135                1140

Glu Glu  Lys Ile Glu Phe Glu  Trp Asn Thr Gly Thr  Asn Val Asp
    1145                1150                1155
```

-continued

```
Thr Lys Lys Met Thr Ser Asn Phe Pro Val Asp Leu Ser Asp Tyr
    1160                1165                1170

Pro Lys Ser Leu His Met Tyr Ala Asn Arg Leu Leu Asp His Arg
    1175                1180                1185

Val Pro Glu Thr Asp Met Thr Phe Arg His Val Gly Ser Lys Leu
    1190                1195                1200

Ile Val Ala Met Ser Ser Trp Leu Gln Lys Ala Ser Gly Ser Leu
    1205                1210                1215

Pro Tyr Thr Gln Thr Leu Gln Asp His Leu Asn Ser Leu Lys Glu
    1220                1225                1230

Phe Asn Leu Gln Asn Met Gly Leu Pro Asp Phe His Ile Pro Glu
    1235                1240                1245

Asn Leu Phe Leu Lys Ser Asp Gly Arg Val Lys Tyr Thr Leu Asn
    1250                1255                1260

Lys Asn Ser Leu Lys Ile Glu Ile Pro Leu Pro Phe Gly Gly Lys
    1265                1270                1275

Ser Ser Arg Asp Leu Lys Met Leu Glu Thr Val Arg Thr Pro Ala
    1280                1285                1290

Leu His Phe Lys Ser Val Gly Phe His Leu Pro Ser Arg Glu Phe
    1295                1300                1305

Gln Val Pro Thr Phe Thr Ile Pro Lys Leu Tyr Gln Leu Gln Val
    1310                1315                1320

Pro Leu Leu Gly Val Leu Asp Leu Ser Thr Asn Val Tyr Ser Asn
    1325                1330                1335

Leu Tyr Asn Trp Ser Ala Ser Tyr Ser Gly Gly Asn Thr Ser Thr
    1340                1345                1350

Asp His Phe Ser Leu Arg Ala Arg Tyr His Met Lys Ala Asp Ser
    1355                1360                1365

Val Val Asp Leu Leu Ser Tyr Asn Val Gln Gly Ser Gly Glu Thr
    1370                1375                1380

Thr Tyr Asp His Lys Asn Thr Phe Thr Leu Ser Cys Asp Gly Ser
    1385                1390                1395

Leu Arg His Lys Phe Leu Asp Ser Asn Ile Lys Phe Ser His Val
    1400                1405                1410

Glu Lys Leu Gly Asn Asn Pro Val Ser Lys Gly Leu Leu Ile Phe
    1415                1420                1425

Asp Ala Ser Ser Ser Trp Gly Pro Gln Met Ser Ala Ser Val His
    1430                1435                1440

Leu Asp Ser Lys Lys Lys Gln His Leu Phe Val Lys Glu Val Lys
    1445                1450                1455

Ile Asp Gly Gln Phe Arg Val Ser Ser Phe Tyr Ala Lys Gly Thr
    1460                1465                1470

Tyr Gly Leu Ser Cys Gln Arg Asp Pro Asn Thr Gly Arg Leu Asn
    1475                1480                1485

Gly Glu Ser Asn Leu Arg Phe Asn Ser Ser Tyr Leu Gln Gly Thr
    1490                1495                1500

Asn Gln Ile Thr Gly Arg Tyr Glu Asp Gly Thr Leu Ser Leu Thr
    1505                1510                1515

Ser Thr Ser Asp Leu Gln Ser Gly Ile Ile Lys Asn Thr Ala Ser
    1520                1525                1530

Leu Lys Tyr Glu Asn Tyr Glu Leu Thr Leu Lys Ser Asp Thr Asn
    1535                1540                1545

Gly Lys Tyr Lys Asn Phe Ala Thr Ser Asn Lys Met Asp Met Thr
```

-continued

```
             1550            1555            1560

Phe Ser Lys Gln Asn Ala Leu Leu Arg Ser Glu Tyr Gln Ala Asp
    1565            1570            1575

Tyr Glu Ser Leu Arg Phe Phe Ser Leu Leu Ser Gly Ser Leu Asn
    1580            1585            1590

Ser His Gly Leu Glu Leu Asn Ala Asp Ile Leu Gly Thr Asp Lys
    1595            1600            1605

Ile Asn Ser Gly Ala His Lys Ala Thr Leu Arg Ile Gly Gln Asp
    1610            1615            1620

Gly Ile Ser Thr Ser Ala Thr Thr Asn Leu Lys Cys Ser Leu Leu
    1625            1630            1635

Val Leu Glu Asn Glu Leu Asn Ala Glu Leu Gly Leu Ser Gly Ala
    1640            1645            1650

Ser Met Lys Leu Thr Thr Asn Gly Arg Phe Arg Glu His Asn Ala
    1655            1660            1665

Lys Phe Ser Leu Asp Gly Lys Ala Ala Leu Thr Glu Leu Ser Leu
    1670            1675            1680

Gly Ser Ala Tyr Gln Ala Met Ile Leu Gly Val Asp Ser Lys Asn
    1685            1690            1695

Ile Phe Asn Phe Lys Val Ser Gln Gly Leu Lys Leu Ser Asn
    1700            1705            1710

Asp Met Met Gly Ser Tyr Ala Glu Met Lys Phe Asp His Thr Asn
    1715            1720            1725

Ser Leu Asn Ile Ala Gly Leu Ser Leu Asp Phe Ser Ser Lys Leu
    1730            1735            1740

Asp Asn Ile Tyr Ser Ser Asp Lys Phe Tyr Lys Gln Thr Val Asn
    1745            1750            1755

Leu Gln Leu Gln Pro Tyr Ser Leu Val Thr Thr Leu Asn Ser Asp
    1760            1765            1770

Leu Lys Tyr Asn Ala Leu Asp Leu Thr Asn Asn Gly Lys Leu Arg
    1775            1780            1785

Leu Glu Pro Leu Lys Leu His Val Ala Gly Asn Leu Lys Gly Ala
    1790            1795            1800

Tyr Gln Asn Asn Glu Ile Lys His Ile Tyr Ala Ile Ser Ser Ala
    1805            1810            1815

Ala Leu Ser Ala Ser Tyr Lys Ala Asp Thr Val Ala Lys Val Gln
    1820            1825            1830

Gly Val Glu Phe Ser His Arg Leu Asn Thr Asp Ile Ala Gly Leu
    1835            1840            1845

Ala Ser Ala Ile Asp Met Ser Thr Asn Tyr Asn Ser Asp Ser Leu
    1850            1855            1860

His Phe Ser Asn Val Phe Arg Ser Val Met Ala Pro Phe Thr Met
    1865            1870            1875

Thr Ile Asp Ala His Thr Asn Gly Asn Gly Lys Leu Ala Leu Trp
    1880            1885            1890

Gly Glu His Thr Gly Gln Leu Tyr Ser Lys Phe Leu Leu Lys Ala
    1895            1900            1905

Glu Pro Leu Ala Phe Thr Phe Ser His Asp Tyr Lys Gly Ser Thr
    1910            1915            1920

Ser His His Leu Val Ser Arg Lys Ser Ile Ser Ala Ala Leu Glu
    1925            1930            1935

His Lys Val Ser Ala Leu Leu Thr Pro Ala Glu Gln Thr Gly Thr
    1940            1945            1950
```

```
Trp Lys Leu Lys Thr Gln Phe Asn Asn Asn Glu Tyr Ser Gln Asp
1955                 1960                 1965

Leu Asp Ala Tyr Asn Thr Lys Asp Lys Ile Gly Val Glu Leu Thr
1970                 1975                 1980

Gly Arg Thr Leu Ala Asp Leu Thr Leu Leu Asp Ser Pro Ile Lys
1985                 1990                 1995

Val Pro Leu Leu Leu Ser Glu Pro Ile Asn Ile Ile Asp Ala Leu
2000                 2005                 2010

Glu Met Arg Asp Ala Val Glu Lys Pro Gln Glu Phe Thr Ile Val
2015                 2020                 2025

Ala Phe Val Lys Tyr Asp Lys Asn Gln Asp Val His Ser Ile Asn
2030                 2035                 2040

Leu Pro Phe Phe Glu Thr Leu Gln Glu Tyr Phe Glu Arg Asn Arg
2045                 2050                 2055

Gln Thr Ile Ile Val Val Glu Asn Val Gln Arg Asn Leu Lys
2060                 2065                 2070

His Ile Asn Ile Asp Gln Phe Val Arg Lys Tyr Arg Ala Ala Leu
2075                 2080                 2085

Gly Lys Leu Pro Gln Gln Ala Asn Asp Tyr Leu Asn Ser Phe Asn
2090                 2095                 2100

Trp Glu Arg Gln Val Ser His Ala Lys Glu Lys Leu Thr Ala Leu
2105                 2110                 2115

Thr Lys Lys Tyr Arg Ile Thr Glu Asn Asp Ile Gln Ile Ala Leu
2120                 2125                 2130

Asp Asp Ala Lys Ile Asn Phe Asn Glu Lys Leu Ser Gln Leu Gln
2135                 2140                 2145

Thr Tyr Met Ile Gln Phe Asp Gln Tyr Ile Lys Asp Ser Tyr Asp
2150                 2155                 2160

Leu His Asp Leu Lys Ile Ala Ile Ala Asn Ile Ile Asp Glu Ile
2165                 2170                 2175

Ile Glu Lys Leu Lys Ser Leu Asp Glu His Tyr His Ile Arg Val
2180                 2185                 2190

Asn Leu Val Lys Thr Ile His Asp Leu His Leu Phe Ile Glu Asn
2195                 2200                 2205

Ile Asp Phe Asn Lys Ser Gly Ser Ser Thr Ala Ser Trp Ile Gln
2210                 2215                 2220

Asn Val Asp Thr Lys Tyr Gln Ile Arg Ile Gln Ile Gln Glu Lys
2225                 2230                 2235

Leu Gln Gln Leu Lys Arg His Ile Gln Asn Ile Asp Ile Gln His
2240                 2245                 2250

Leu Ala Gly Lys Leu Lys Gln His Ile Glu Ala Ile Asp Val Arg
2255                 2260                 2265

Val Leu Leu Asp Gln Leu Gly Thr Thr Ile Ser Phe Glu Arg Ile
2270                 2275                 2280

Asn Asp Val Leu Glu His Val Lys His Phe Val Ile Asn Leu Ile
2285                 2290                 2295

Gly Asp Phe Glu Val Ala Glu Lys Ile Asn Ala Phe Arg Ala Lys
2300                 2305                 2310

Val His Glu Leu Ile Glu Arg Tyr Glu Val Asp Gln Gln Ile Gln
2315                 2320                 2325

Val Leu Met Asp Lys Leu Val Glu Leu Thr His Gln Tyr Lys Leu
2330                 2335                 2340

Lys Glu Thr Ile Gln Lys Leu Ser Asn Val Leu Gln Gln Val Lys
2345                 2350                 2355
```

```
Ile Lys Asp Tyr Phe Glu Lys Leu Val Gly Phe Ile Asp Asp Ala
    2360            2365            2370

Val Lys Lys Leu Asn Glu Leu Ser Phe Lys Thr Phe Ile Glu Asp
    2375            2380            2385

Val Asn Lys Phe Leu Asp Met Leu Ile Lys Lys Leu Lys Ser Phe
    2390            2395            2400

Asp Tyr His Gln Phe Val Asp Glu Thr Asn Asp Lys Ile Arg Glu
    2405            2410            2415

Val Thr Gln Arg Leu Asn Gly Glu Ile Gln Ala Leu Glu Leu Pro
    2420            2425            2430

Gln Lys Ala Glu Ala Leu Lys Leu Phe Leu Glu Glu Thr Lys Ala
    2435            2440            2445

Thr Val Ala Val Tyr Leu Glu Ser Leu Gln Asp Thr Lys Ile Thr
    2450            2455            2460

Leu Ile Ile Asn Trp Leu Gln Glu Ala Leu Ser Ser Ala Ser Leu
    2465            2470            2475

Ala His Met Lys Ala Lys Phe Arg Glu Thr Leu Glu Asp Thr Arg
    2480            2485            2490

Asp Arg Met Tyr Gln Met Asp Ile Gln Gln Glu Leu Gln Arg Tyr
    2495            2500            2505

Leu Ser Leu Val Gly Gln Val Tyr Ser Thr Leu Val Thr Tyr Ile
    2510            2515            2520

Ser Asp Trp Trp Thr Leu Ala Ala Lys Asn Leu Thr Asp Phe Ala
    2525            2530            2535

Glu Gln Tyr Ser Ile Gln Asp Trp Ala Lys Arg Met Lys Ala Leu
    2540            2545            2550

Val Glu Gln Gly Phe Thr Val Pro Glu Ile Lys Thr Ile Leu Gly
    2555            2560            2565

Thr Met Pro Ala Phe Glu Val Ser Leu Gln Ala Leu Gln Lys Ala
    2570            2575            2580

Thr Phe Gln Thr Pro Asp Phe Ile Val Pro Leu Thr Asp Leu Arg
    2585            2590            2595

Ile Pro Ser Val Gln Ile Asn Phe Lys Asp Leu Lys Asn Ile Lys
    2600            2605            2610

Ile Pro Ser Arg Phe Ser Thr Pro Glu Phe Thr Ile Leu Asn Thr
    2615            2620            2625

Phe His Ile Pro Ser Phe Thr Ile Asp Phe Val Glu Met Lys Val
    2630            2635            2640

Lys Ile Ile Arg Thr Ile Asp Gln Met Gln Asn Ser Glu Leu Gln
    2645            2650            2655

Trp Pro Val Pro Asp Ile Tyr Leu Arg Asp Leu Lys Val Glu Asp
    2660            2665            2670

Ile Pro Leu Ala Arg Ile Thr Leu Pro Asp Phe Arg Leu Pro Glu
    2675            2680            2685

Ile Ala Ile Pro Glu Phe Ile Ile Pro Thr Leu Asn Leu Asn Asp
    2690            2695            2700

Phe Gln Val Pro Asp Leu His Ile Pro Glu Phe Gln Leu Pro His
    2705            2710            2715

Ile Ser His Thr Ile Glu Val Pro Thr Phe Gly Lys Leu Tyr Ser
    2720            2725            2730

Ile Leu Lys Ile Gln Ser Pro Leu Phe Thr Leu Asp Ala Asn Ala
    2735            2740            2745

Asp Ile Gly Asn Gly Thr Thr Ser Ala Asn Glu Ala Gly Ile Ala
```

-continued

```
            2750              2755              2760

Ala Ser Ile Thr Ala Lys Gly Glu Ser Lys Leu Glu Val Leu Asn
        2765              2770              2775

Phe Asp Phe Gln Ala Asn Ala Gln Leu Ser Asn Pro Lys Ile Asn
        2780              2785              2790

Pro Leu Ala Leu Lys Glu Ser Val Lys Phe Ser Ser Lys Tyr Leu
        2795              2800              2805

Arg Thr Glu His Gly Ser Glu Met Leu Phe Phe Gly Asn Ala Ile
        2810              2815              2820

Glu Gly Lys Ser Asn Thr Val Ala Ser Leu His Thr Glu Lys Asn
        2825              2830              2835

Thr Leu Glu Leu Ser Asn Gly Val Ile Val Lys Ile Asn Asn Gln
        2840              2845              2850

Leu Thr Leu Asp Ser Asn Thr Lys Tyr Phe His Lys Leu Asn Ile
        2855              2860              2865

Pro Lys Leu Asp Phe Ser Ser Gln Ala Asp Leu Arg Asn Glu Ile
        2870              2875              2880

Lys Thr Leu Leu Lys Ala Gly His Ile Ala Trp Thr Ser Ser Gly
        2885              2890              2895

Lys Gly Ser Trp Lys Trp Ala Cys Pro Arg Phe Ser Asp Glu Gly
        2900              2905              2910

Thr His Glu Ser Gln Ile Ser Phe Thr Ile Glu Gly Pro Leu Thr
        2915              2920              2925

Ser Phe Gly Leu Ser Asn Lys Ile Asn Ser Lys His Leu Arg Val
        2930              2935              2940

Asn Gln Asn Leu Val Tyr Glu Ser Gly Ser Leu Asn Phe Ser Lys
        2945              2950              2955

Leu Glu Ile Gln Ser Gln Val Asp Ser Gln His Val Gly His Ser
        2960              2965              2970

Val Leu Thr Ala Lys Gly Met Ala Leu Phe Gly Glu Gly Lys Ala
        2975              2980              2985

Glu Phe Thr Gly Arg His Asp Ala His Leu Asn Gly Lys Val Ile
        2990              2995              3000

Gly Thr Leu Lys Asn Ser Leu Phe Phe Ser Ala Gln Pro Phe Glu
        3005              3010              3015

Ile Thr Ala Ser Thr Asn Asn Glu Gly Asn Leu Lys Val Arg Phe
        3020              3025              3030

Pro Leu Arg Leu Thr Gly Lys Ile Asp Phe Leu Asn Asn Tyr Ala
        3035              3040              3045

Leu Phe Leu Ser Pro Ser Ala Gln Gln Ala Ser Trp Gln Val Ser
        3050              3055              3060

Ala Arg Phe Asn Gln Tyr Lys Tyr Asn Gln Asn Phe Ser Ala Gly
        3065              3070              3075

Asn Asn Glu Asn Ile Met Glu Ala His Val Gly Ile Asn Gly Glu
        3080              3085              3090

Ala Asn Leu Asp Phe Leu Asn Ile Pro Leu Thr Ile Pro Glu Met
        3095              3100              3105

Arg Leu Pro Tyr Thr Ile Ile Thr Thr Pro Pro Leu Lys Asp Phe
        3110              3115              3120

Ser Leu Trp Glu Lys Thr Gly Leu Lys Glu Phe Leu Lys Thr Thr
        3125              3130              3135

Lys Gln Ser Phe Asp Leu Ser Val Lys Ala Gln Tyr Lys Lys Asn
        3140              3145              3150
```

-continued

Lys His Arg His Ser Ile Thr Asn Pro Leu Ala Val Leu Cys Glu
3155                3160              3165

Phe Ile Ser Gln Ser Ile Lys Ser Phe Asp Arg His Phe Glu Lys
3170                3175              3180

Asn Arg Asn Asn Ala Leu Asp Phe Val Thr Lys Ser Tyr Asn Glu
3185                3190              3195

Thr Lys Ile Lys Phe Asp Lys Tyr Lys Ala Glu Lys Ser His Asp
3200                3205              3210

Glu Leu Pro Arg Thr Phe Gln Ile Pro Gly Tyr Thr Val Pro Val
3215                3220              3225

Val Asn Val Glu Val Ser Pro Phe Thr Ile Glu Met Ser Ala Phe
3230                3235              3240

Gly Tyr Val Phe Pro Lys Ala Val Ser Met Pro Ser Phe Ser Ile
3245                3250              3255

Leu Gly Ser Asp Val Arg Val Pro Ser Tyr Thr Leu Ile Leu Pro
3260                3265              3270

Ser Leu Glu Leu Pro Val Leu His Val Pro Arg Asn Leu Lys Leu
3275                3280              3285

Ser Leu Pro His Phe Lys Glu Leu Cys Thr Ile Ser His Ile Phe
3290                3295              3300

Ile Pro Ala Met Gly Asn Ile Thr Tyr Asp Phe Ser Phe Lys Ser
3305                3310              3315

Ser Val Ile Thr Leu Asn Thr Asn Ala Glu Leu Phe Asn Gln Ser
3320                3325              3330

Asp Ile Val Ala His Leu Leu Ser Ser Ser Ser Val Ile Asp
3335                3340              3345

Ala Leu Gln Tyr Lys Leu Glu Gly Thr Thr Arg Leu Thr Arg Lys
3350                3355              3360

Arg Gly Leu Lys Leu Ala Thr Ala Leu Ser Leu Ser Asn Lys Phe
3365                3370              3375

Val Glu Gly Ser His Asn Ser Thr Val Ser Leu Thr Thr Lys Asn
3380                3385              3390

Met Glu Val Ser Val Ala Lys Thr Thr Lys Ala Glu Ile Pro Ile
3395                3400              3405

Leu Arg Met Asn Phe Lys Gln Glu Leu Asn Gly Asn Thr Lys Ser
3410                3415              3420

Lys Pro Thr Val Ser Ser Ser Met Glu Phe Lys Tyr Asp Phe Asn
3425                3430              3435

Ser Ser Met Leu Tyr Ser Thr Ala Lys Gly Ala Val Asp His Lys
3440                3445              3450

Leu Ser Leu Glu Ser Leu Thr Ser Tyr Phe Ser Ile Glu Ser Ser
3455                3460              3465

Thr Lys Gly Asp Val Lys Gly Ser Val Leu Ser Arg Glu Tyr Ser
3470                3475              3480

Gly Thr Ile Ala Ser Glu Ala Asn Thr Tyr Leu Asn Ser Lys Ser
3485                3490              3495

Thr Arg Ser Ser Val Lys Leu Gln Gly Thr Ser Lys Ile Asp Asp
3500                3505              3510

Ile Trp Asn Leu Glu Val Lys Glu Asn Phe Ala Gly Glu Ala Thr
3515                3520              3525

Leu Gln Arg Ile Tyr Ser Leu Trp Glu His Ser Thr Lys Asn His
3530                3535              3540

Leu Gln Leu Glu Gly Leu Phe Phe Thr Asn Gly Glu His Thr Ser
3545                3550              3555

```
Lys Ala Thr Leu Glu Leu Ser Pro Trp Gln Met Ser Ala Leu Val
    3560            3565            3570

Gln Val His Ala Ser Gln Pro Ser Ser Phe His Asp Phe Pro Asp
    3575            3580            3585

Leu Gly Gln Glu Val Ala Leu Asn Ala Asn Thr Lys Asn Gln Lys
    3590            3595            3600

Ile Arg Trp Lys Asn Glu Val Arg Ile His Ser Gly Ser Phe Gln
    3605            3610            3615

Ser Gln Val Glu Leu Ser Asn Asp Gln Glu Lys Ala His Leu Asp
    3620            3625            3630

Ile Ala Gly Ser Leu Glu Gly His Leu Arg Phe Leu Lys Asn Ile
    3635            3640            3645

Ile Leu Pro Val Tyr Asp Lys Ser Leu Trp Asp Phe Leu Lys Leu
    3650            3655            3660

Asp Val Thr Thr Ser Ile Gly Arg Arg Gln His Leu Arg Val Ser
    3665            3670            3675

Thr Ala Phe Val Tyr Thr Lys Asn Pro Asn Gly Tyr Ser Phe Ser
    3680            3685            3690

Ile Pro Val Lys Val Leu Ala Asp Lys Phe Ile Thr Pro Gly Leu
    3695            3700            3705

Lys Leu Asn Asp Leu Asn Ser Val Leu Val Met Pro Thr Phe His
    3710            3715            3720

Val Pro Phe Thr Asp Leu Gln Val Pro Ser Cys Lys Leu Asp Phe
    3725            3730            3735

Arg Glu Ile Gln Ile Tyr Lys Lys Leu Arg Thr Ser Ser Phe Ala
    3740            3745            3750

Leu Asn Leu Pro Thr Leu Pro Glu Val Lys Phe Pro Glu Val Asp
    3755            3760            3765

Val Leu Thr Lys Tyr Ser Gln Pro Glu Asp Ser Leu Ile Pro Phe
    3770            3775            3780

Phe Glu Ile Thr Val Pro Glu Ser Gln Leu Thr Val Ser Gln Phe
    3785            3790            3795

Thr Leu Pro Lys Ser Val Ser Asp Gly Ile Ala Ala Leu Asp Leu
    3800            3805            3810

Asn Ala Val Ala Asn Lys Ile Ala Asp Phe Glu Leu Pro Thr Ile
    3815            3820            3825

Ile Val Pro Glu Gln Thr Ile Glu Ile Pro Ser Ile Lys Phe Ser
    3830            3835            3840

Val Pro Ala Gly Ile Val Ile Pro Ser Phe Gln Ala Leu Thr Ala
    3845            3850            3855

Arg Phe Glu Val Asp Ser Pro Val Tyr Asn Ala Thr Trp Ser Ala
    3860            3865            3870

Ser Leu Lys Asn Lys Ala Asp Tyr Val Glu Thr Val Leu Asp Ser
    3875            3880            3885

Thr Cys Ser Ser Thr Val Gln Phe Leu Glu Tyr Glu Leu Asn Val
    3890            3895            3900

Leu Gly Thr His Lys Ile Glu Asp Gly Thr Leu Ala Ser Lys Thr
    3905            3910            3915

Lys Gly Thr Leu Ala His Arg Asp Phe Ser Ala Glu Tyr Glu Glu
    3920            3925            3930

Asp Gly Lys Phe Glu Gly Leu Gln Glu Trp Glu Gly Lys Ala His
    3935            3940            3945

Leu Asn Ile Lys Ser Pro Ala Phe Thr Asp Leu His Leu Arg Tyr
```

```
                3950              3955                3960
Gln Lys Asp Lys Lys Gly Ile Ser Thr Ser Ala Ala Ser Pro Ala
    3965            3970                3975
Val Gly Thr Val Gly Met Asp Met Asp Glu Asp Asp Phe Ser
    3980            3985                3990
Lys Trp Asn Phe Tyr Tyr Ser Pro Gln Ser Ser Pro Asp Lys Lys
    3995            4000                4005
Leu Thr Ile Phe Lys Thr Glu Leu Arg Val Arg Glu Ser Asp Glu
    4010            4015                4020
Glu Thr Gln Ile Lys Val Asn Trp Glu Glu Glu Ala Ala Ser Gly
    4025            4030                4035
Leu Leu Thr Ser Leu Lys Asp Asn Val Pro Lys Ala Thr Gly Val
    4040            4045                4050
Leu Tyr Asp Tyr Val Asn Lys Tyr His Trp Glu His Thr Gly Leu
    4055            4060                4065
Thr Leu Arg Glu Val Ser Ser Lys Leu Arg Arg Asn Leu Gln Asn
    4070            4075                4080
Asn Ala Glu Trp Val Tyr Gln Gly Ala Ile Arg Gln Ile Asp Asp
    4085            4090                4095
Ile Asp Val Arg Phe Gln Lys Ala Ala Ser Gly Thr Thr Gly Thr
    4100            4105                4110
Tyr Gln Glu Trp Lys Asp Lys Ala Gln Asn Leu Tyr Gln Glu Leu
    4115            4120                4125
Leu Thr Gln Glu Gly Gln Ala Ser Phe Gln Gly Leu Lys Asp Asn
    4130            4135                4140
Val Phe Asp Gly Leu Val Arg Val Thr Gln Lys Phe His Met Lys
    4145            4150                4155
Val Lys His Leu Ile Asp Ser Leu Ile Asp Phe Leu Asn Phe Pro
    4160            4165                4170
Arg Phe Gln Phe Pro Gly Lys Pro Gly Ile Tyr Thr Arg Glu Glu
    4175            4180                4185
Leu Cys Thr Met Phe Ile Arg Glu Val Gly Thr Val Leu Ser Gln
    4190            4195                4200
Val Tyr Ser Lys Val His Asn Gly Ser Glu Ile Leu Phe Ser Tyr
    4205            4210                4215
Phe Gln Asp Leu Val Ile Thr Leu Pro Phe Glu Leu Arg Lys His
    4220            4225                4230
Lys Leu Ile Asp Val Ile Ser Met Tyr Arg Glu Leu Leu Lys Asp
    4235            4240                4245
Leu Ser Lys Glu Ala Gln Glu Val Phe Lys Ala Ile Gln Ser Leu
    4250            4255                4260
Lys Thr Thr Glu Val Leu Arg Asn Leu Gln Asp Leu Leu Gln Phe
    4265            4270                4275
Ile Phe Gln Leu Ile Glu Asp Asn Ile Lys Gln Leu Lys Glu Met
    4280            4285                4290
Lys Phe Thr Tyr Leu Ile Asn Tyr Ile Gln Asp Glu Ile Asn Thr
    4295            4300                4305
Ile Phe Asn Asp Tyr Ile Pro Tyr Val Phe Lys Leu Leu Lys Glu
    4310            4315                4320
Asn Leu Cys Leu Asn Leu His Lys Phe Asn Glu Phe Ile Gln Asn
    4325            4330                4335
Glu Leu Gln Glu Ala Ser Gln Glu Leu Gln Gln Ile His Gln Tyr
    4340            4345                4350
```

-continued

```
Ile Met Ala Leu Arg Glu Glu Tyr Phe Asp Pro Ser Ile Val Gly
    4355                4360                4365

Trp Thr Val Lys Tyr Tyr Glu Leu Glu Lys Ile Val Ser Leu
    4370                4375                4380

Ile Lys Asn Leu Leu Val Ala Leu Lys Asp Phe His Ser Glu Tyr
    4385                4390                4395

Ile Val Ser Ala Ser Asn Phe Thr Ser Gln Leu Ser Ser Gln Val
    4400                4405                4410

Glu Gln Phe Leu His Arg Asn Ile Gln Glu Tyr Leu Ser Ile Leu
    4415                4420                4425

Thr Asp Pro Asp Gly Lys Gly Lys Glu Lys Ile Ala Glu Leu Ser
    4430                4435                4440

Ala Thr Ala Gln Glu Ile Ile Lys Ser Gln Ala Ile Ala Thr Lys
    4445                4450                4455

Lys Ile Ile Ser Asp Tyr His Gln Gln Phe Arg Tyr Lys Leu Gln
    4460                4465                4470

Asp Phe Ser Asp Gln Leu Ser Asp Tyr Tyr Glu Lys Phe Ile Ala
    4475                4480                4485

Glu Ser Lys Arg Leu Ile Asp Leu Ser Ile Gln Asn Tyr His Thr
    4490                4495                4500

Phe Leu Ile Tyr Ile Thr Glu Leu Leu Lys Lys Leu Gln Ser Thr
    4505                4510                4515

Thr Val Met Asn Pro Tyr Met Lys Leu Ala Pro Gly Glu Leu Thr
    4520                4525                4530

Ile Ile Leu
    4535

<210> SEQ ID NO 33
<211> LENGTH: 2152
<212> TYPE: PRT
<213> ORGANISM: Homo sapiens
<220> FEATURE:
<221> NAME/KEY: MISC_FEATURE
<223> OTHER INFORMATION: APO B48 Region 28-2179 of preprotein Acc. No.
      NP_000375.1

<400> SEQUENCE: 33

Glu Glu Glu Met Leu Glu Asn Val Ser Leu Val Cys Pro Lys Asp Ala
1               5                   10                  15

Thr Arg Phe Lys His Leu Arg Lys Tyr Thr Tyr Asn Tyr Glu Ala Glu
            20                  25                  30

Ser Ser Ser Gly Val Pro Gly Thr Ala Asp Ser Arg Ser Ala Thr Arg
        35                  40                  45

Ile Asn Cys Lys Val Glu Leu Glu Val Pro Gln Leu Cys Ser Phe Ile
    50                  55                  60

Leu Lys Thr Ser Gln Cys Thr Leu Lys Glu Val Tyr Gly Phe Asn Pro
65                  70                  75                  80

Glu Gly Lys Ala Leu Leu Lys Lys Thr Lys Asn Ser Glu Glu Phe Ala
                85                  90                  95

Ala Ala Met Ser Arg Tyr Glu Leu Lys Leu Ala Ile Pro Glu Gly Lys
            100                 105                 110

Gln Val Phe Leu Tyr Pro Glu Lys Asp Glu Pro Thr Tyr Ile Leu Asn
        115                 120                 125

Ile Lys Arg Gly Ile Ile Ser Ala Leu Leu Val Pro Pro Glu Thr Glu
    130                 135                 140

Glu Ala Lys Gln Val Leu Phe Leu Asp Thr Val Tyr Gly Asn Cys Ser
145                 150                 155                 160
```

-continued

Thr His Phe Thr Val Lys Thr Arg Lys Gly Asn Val Ala Thr Glu Ile
            165                 170                 175

Ser Thr Glu Arg Asp Leu Gly Gln Cys Asp Arg Phe Lys Pro Ile Arg
        180                 185                 190

Thr Gly Ile Ser Pro Leu Ala Leu Ile Lys Gly Met Thr Arg Pro Leu
            195                 200                 205

Ser Thr Leu Ile Ser Ser Gln Ser Cys Gln Tyr Thr Leu Asp Ala
    210                 215                 220

Lys Arg Lys His Val Ala Glu Ala Ile Cys Lys Glu Gln His Leu Phe
225                 230                 235                 240

Leu Pro Phe Ser Tyr Asn Asn Lys Tyr Gly Met Val Ala Gln Val Thr
                245                 250                 255

Gln Thr Leu Lys Leu Glu Asp Thr Pro Lys Ile Asn Ser Arg Phe Phe
            260                 265                 270

Gly Glu Gly Thr Lys Lys Met Gly Leu Ala Phe Glu Ser Thr Lys Ser
            275                 280                 285

Thr Ser Pro Pro Lys Gln Ala Glu Ala Val Leu Lys Thr Leu Gln Glu
    290                 295                 300

Leu Lys Lys Leu Thr Ile Ser Glu Gln Asn Ile Gln Arg Ala Asn Leu
305                 310                 315                 320

Phe Asn Lys Leu Val Thr Glu Leu Arg Gly Leu Ser Asp Glu Ala Val
                325                 330                 335

Thr Ser Leu Leu Pro Gln Leu Ile Glu Val Ser Ser Pro Ile Thr Leu
            340                 345                 350

Gln Ala Leu Val Gln Cys Gly Gln Pro Gln Cys Ser Thr His Ile Leu
            355                 360                 365

Gln Trp Leu Lys Arg Val His Ala Asn Pro Leu Leu Ile Asp Val Val
    370                 375                 380

Thr Tyr Leu Val Ala Leu Ile Pro Glu Pro Ser Ala Gln Gln Leu Arg
385                 390                 395                 400

Glu Ile Phe Asn Met Ala Arg Asp Gln Arg Ser Arg Ala Thr Leu Tyr
                405                 410                 415

Ala Leu Ser His Ala Val Asn Asn Tyr His Lys Thr Asn Pro Thr Gly
            420                 425                 430

Thr Gln Glu Leu Leu Asp Ile Ala Asn Tyr Leu Met Glu Gln Ile Gln
    435                 440                 445

Asp Asp Cys Thr Gly Asp Glu Asp Tyr Thr Tyr Leu Ile Leu Arg Val
    450                 455                 460

Ile Gly Asn Met Gly Gln Thr Met Glu Gln Leu Thr Pro Glu Leu Lys
465                 470                 475                 480

Ser Ser Ile Leu Lys Cys Val Gln Ser Thr Lys Pro Ser Leu Met Ile
                485                 490                 495

Gln Lys Ala Ala Ile Gln Ala Leu Arg Lys Met Glu Pro Lys Asp Lys
            500                 505                 510

Asp Gln Glu Val Leu Leu Gln Thr Phe Leu Asp Asp Ala Ser Pro Gly
    515                 520                 525

Asp Lys Arg Leu Ala Ala Tyr Leu Met Leu Met Arg Ser Pro Ser Gln
    530                 535                 540

Ala Asp Ile Asn Lys Ile Val Gln Ile Leu Pro Trp Glu Gln Asn Glu
545                 550                 555                 560

Gln Val Lys Asn Phe Val Ala Ser His Ile Ala Asn Ile Leu Asn Ser
                565                 570                 575

Glu Glu Leu Asp Ile Gln Asp Leu Lys Lys Leu Val Lys Glu Ala Leu

-continued

```
                580                 585                 590
Lys Glu Ser Gln Leu Pro Thr Val Met Asp Phe Arg Lys Phe Ser Arg
            595                 600                 605

Asn Tyr Gln Leu Tyr Lys Ser Val Ser Leu Pro Ser Leu Asp Pro Ala
        610                 615                 620

Ser Ala Lys Ile Glu Gly Asn Leu Ile Phe Asp Pro Asn Asn Tyr Leu
625                 630                 635                 640

Pro Lys Glu Ser Met Leu Lys Thr Thr Leu Thr Ala Phe Gly Phe Ala
                645                 650                 655

Ser Ala Asp Leu Ile Glu Ile Gly Leu Glu Gly Lys Gly Phe Glu Pro
            660                 665                 670

Thr Leu Glu Ala Leu Phe Gly Lys Gln Gly Phe Phe Pro Asp Ser Val
        675                 680                 685

Asn Lys Ala Leu Tyr Trp Val Asn Gly Gln Val Pro Asp Gly Val Ser
    690                 695                 700

Lys Val Leu Val Asp His Phe Gly Tyr Thr Lys Asp Asp Lys His Glu
705                 710                 715                 720

Gln Asp Met Val Asn Gly Ile Met Leu Ser Val Glu Lys Leu Ile Lys
                725                 730                 735

Asp Leu Lys Ser Lys Glu Val Pro Glu Ala Arg Ala Tyr Leu Arg Ile
            740                 745                 750

Leu Gly Glu Glu Leu Gly Phe Ala Ser Leu His Asp Leu Gln Leu Leu
        755                 760                 765

Gly Lys Leu Leu Leu Met Gly Ala Arg Thr Leu Gln Gly Ile Pro Gln
    770                 775                 780

Met Ile Gly Glu Val Ile Arg Lys Gly Ser Lys Asn Asp Phe Phe Leu
785                 790                 795                 800

His Tyr Ile Phe Met Glu Asn Ala Phe Glu Leu Pro Thr Gly Ala Gly
                805                 810                 815

Leu Gln Leu Gln Ile Ser Ser Gly Val Ile Ala Pro Gly Ala Lys
            820                 825                 830

Ala Gly Val Lys Leu Glu Val Ala Asn Met Gln Ala Glu Leu Val Ala
        835                 840                 845

Lys Pro Ser Val Ser Val Glu Phe Val Thr Asn Met Gly Ile Ile Ile
    850                 855                 860

Pro Asp Phe Ala Arg Ser Gly Val Gln Met Asn Thr Asn Phe Phe His
865                 870                 875                 880

Glu Ser Gly Leu Glu Ala His Val Ala Leu Lys Ala Gly Lys Leu Lys
                885                 890                 895

Phe Ile Ile Pro Ser Pro Lys Arg Pro Val Lys Leu Leu Ser Gly Gly
            900                 905                 910

Asn Thr Leu His Leu Val Ser Thr Thr Lys Thr Glu Val Ile Pro Pro
        915                 920                 925

Leu Ile Glu Asn Arg Gln Ser Trp Ser Val Cys Lys Gln Val Phe Pro
    930                 935                 940

Gly Leu Asn Tyr Cys Thr Ser Gly Ala Tyr Ser Asn Ala Ser Ser Thr
945                 950                 955                 960

Asp Ser Ala Ser Tyr Tyr Pro Leu Thr Gly Asp Thr Arg Leu Glu Leu
                965                 970                 975

Glu Leu Arg Pro Thr Gly Glu Ile Glu Gln Tyr Ser Val Ser Ala Thr
            980                 985                 990

Tyr Glu Leu Gln Arg Glu Asp Arg Ala Leu Val Asp Thr Leu Lys Phe
        995                 1000                1005
```

-continued

| | | | | | | | | | | | |
|---|---|---|---|---|---|---|---|---|---|---|---|
| Val | Thr | Gln | Ala | Glu | Gly | Ala | Lys | Gln | Thr | Glu | Ala | Thr | Met | Thr |
| | 1010 | | | | 1015 | | | | 1020 | | |

Val Thr Gln Ala Glu Gly Ala Lys Gln Thr Glu Ala Thr Met Thr
        1010                1015                1020

Phe Lys Tyr Asn Arg Gln Ser Met Thr Leu Ser Ser Glu Val Gln
        1025                1030                1035

Ile Pro Asp Phe Asp Val Asp Leu Gly Thr Ile Leu Arg Val Asn
        1040                1045                1050

Asp Glu Ser Thr Glu Gly Lys Thr Ser Tyr Arg Leu Thr Leu Asp
        1055                1060                1065

Ile Gln Asn Lys Lys Ile Thr Glu Val Ala Leu Met Gly His Leu
        1070                1075                1080

Ser Cys Asp Thr Lys Glu Glu Arg Lys Ile Lys Gly Val Ile Ser
        1085                1090                1095

Ile Pro Arg Leu Gln Ala Glu Ala Arg Ser Glu Ile Leu Ala His
        1100                1105                1110

Trp Ser Pro Ala Lys Leu Leu Leu Gln Met Asp Ser Ser Ala Thr
        1115                1120                1125

Ala Tyr Gly Ser Thr Val Ser Lys Arg Val Ala Trp His Tyr Asp
        1130                1135                1140

Glu Glu Lys Ile Glu Phe Glu Trp Asn Thr Gly Thr Asn Val Asp
        1145                1150                1155

Thr Lys Lys Met Thr Ser Asn Phe Pro Val Asp Leu Ser Asp Tyr
        1160                1165                1170

Pro Lys Ser Leu His Met Tyr Ala Asn Arg Leu Leu Asp His Arg
        1175                1180                1185

Val Pro Glu Thr Asp Met Thr Phe Arg His Val Gly Ser Lys Leu
        1190                1195                1200

Ile Val Ala Met Ser Ser Trp Leu Gln Lys Ala Ser Gly Ser Leu
        1205                1210                1215

Pro Tyr Thr Gln Thr Leu Gln Asp His Leu Asn Ser Leu Lys Glu
        1220                1225                1230

Phe Asn Leu Gln Asn Met Gly Leu Pro Asp Phe His Ile Pro Glu
        1235                1240                1245

Asn Leu Phe Leu Lys Ser Asp Gly Arg Val Lys Tyr Thr Leu Asn
        1250                1255                1260

Lys Asn Ser Leu Lys Ile Glu Ile Pro Leu Pro Phe Gly Gly Lys
        1265                1270                1275

Ser Ser Arg Asp Leu Lys Met Leu Glu Thr Val Arg Thr Pro Ala
        1280                1285                1290

Leu His Phe Lys Ser Val Gly Phe His Leu Pro Ser Arg Glu Phe
        1295                1300                1305

Gln Val Pro Thr Phe Thr Ile Pro Lys Leu Tyr Gln Leu Gln Val
        1310                1315                1320

Pro Leu Leu Gly Val Leu Asp Leu Ser Thr Asn Val Tyr Ser Asn
        1325                1330                1335

Leu Tyr Asn Trp Ser Ala Ser Tyr Ser Gly Gly Asn Thr Ser Thr
        1340                1345                1350

Asp His Phe Ser Leu Arg Ala Arg Tyr His Met Lys Ala Asp Ser
        1355                1360                1365

Val Val Asp Leu Leu Ser Tyr Asn Val Gln Gly Ser Gly Glu Thr
        1370                1375                1380

Thr Tyr Asp His Lys Asn Thr Phe Thr Leu Ser Cys Asp Gly Ser
        1385                1390                1395

Leu Arg His Lys Phe Leu Asp Ser Asn Ile Lys Phe Ser His Val
        1400                1405                1410

-continued

Glu Lys Leu Gly Asn Asn Pro Val Ser Lys Gly Leu Leu Ile Phe
    1415                1420                1425

Asp Ala Ser Ser Ser Trp Gly Pro Gln Met Ser Ala Ser Val His
    1430                1435                1440

Leu Asp Ser Lys Lys Lys Gln His Leu Phe Val Lys Glu Val Lys
    1445                1450                1455

Ile Asp Gly Gln Phe Arg Val Ser Ser Phe Tyr Ala Lys Gly Thr
    1460                1465                1470

Tyr Gly Leu Ser Cys Gln Arg Asp Pro Asn Thr Gly Arg Leu Asn
    1475                1480                1485

Gly Glu Ser Asn Leu Arg Phe Asn Ser Ser Tyr Leu Gln Gly Thr
    1490                1495                1500

Asn Gln Ile Thr Gly Arg Tyr Glu Asp Gly Thr Leu Ser Leu Thr
    1505                1510                1515

Ser Thr Ser Asp Leu Gln Ser Gly Ile Ile Lys Asn Thr Ala Ser
    1520                1525                1530

Leu Lys Tyr Glu Asn Tyr Glu Leu Thr Leu Lys Ser Asp Thr Asn
    1535                1540                1545

Gly Lys Tyr Lys Asn Phe Ala Thr Ser Asn Lys Met Asp Met Thr
    1550                1555                1560

Phe Ser Lys Gln Asn Ala Leu Leu Arg Ser Glu Tyr Gln Ala Asp
    1565                1570                1575

Tyr Glu Ser Leu Arg Phe Phe Ser Leu Leu Ser Gly Ser Leu Asn
    1580                1585                1590

Ser His Gly Leu Glu Leu Asn Ala Asp Ile Leu Gly Thr Asp Lys
    1595                1600                1605

Ile Asn Ser Gly Ala His Lys Ala Thr Leu Arg Ile Gly Gln Asp
    1610                1615                1620

Gly Ile Ser Thr Ser Ala Thr Thr Asn Leu Lys Cys Ser Leu Leu
    1625                1630                1635

Val Leu Glu Asn Glu Leu Asn Ala Glu Leu Gly Leu Ser Gly Ala
    1640                1645                1650

Ser Met Lys Leu Thr Thr Asn Gly Arg Phe Arg Glu His Asn Ala
    1655                1660                1665

Lys Phe Ser Leu Asp Gly Lys Ala Ala Leu Thr Glu Leu Ser Leu
    1670                1675                1680

Gly Ser Ala Tyr Gln Ala Met Ile Leu Gly Val Asp Ser Lys Asn
    1685                1690                1695

Ile Phe Asn Phe Lys Val Ser Gln Glu Gly Leu Lys Leu Ser Asn
    1700                1705                1710

Asp Met Met Gly Ser Tyr Ala Glu Met Lys Phe Asp His Thr Asn
    1715                1720                1725

Ser Leu Asn Ile Ala Gly Leu Ser Leu Asp Phe Ser Ser Lys Leu
    1730                1735                1740

Asp Asn Ile Tyr Ser Ser Asp Lys Phe Tyr Lys Gln Thr Val Asn
    1745                1750                1755

Leu Gln Leu Gln Pro Tyr Ser Leu Val Thr Thr Leu Asn Ser Asp
    1760                1765                1770

Leu Lys Tyr Asn Ala Leu Asp Leu Thr Asn Asn Gly Lys Leu Arg
    1775                1780                1785

Leu Glu Pro Leu Lys Leu His Val Ala Gly Asn Leu Lys Gly Ala
    1790                1795                1800

Tyr Gln Asn Asn Glu Ile Lys His Ile Tyr Ala Ile Ser Ser Ala

```
                1805                1810                1815

Ala Leu Ser Ala Ser Tyr Lys Ala Asp Thr Val Ala Lys Val Gln
    1820                1825                1830

Gly Val Glu Phe Ser His Arg Leu Asn Thr Asp Ile Ala Gly Leu
    1835                1840                1845

Ala Ser Ala Ile Asp Met Ser Thr Asn Tyr Asn Ser Asp Ser Leu
    1850                1855                1860

His Phe Ser Asn Val Phe Arg Ser Val Met Ala Pro Phe Thr Met
    1865                1870                1875

Thr Ile Asp Ala His Thr Asn Gly Asn Gly Lys Leu Ala Leu Trp
    1880                1885                1890

Gly Glu His Thr Gly Gln Leu Tyr Ser Lys Phe Leu Leu Lys Ala
    1895                1900                1905

Glu Pro Leu Ala Phe Thr Phe Ser His Asp Tyr Lys Gly Ser Thr
    1910                1915                1920

Ser His His Leu Val Ser Arg Lys Ser Ile Ser Ala Ala Leu Glu
    1925                1930                1935

His Lys Val Ser Ala Leu Leu Thr Pro Ala Glu Gln Thr Gly Thr
    1940                1945                1950

Trp Lys Leu Lys Thr Gln Phe Asn Asn Asn Glu Tyr Ser Gln Asp
    1955                1960                1965

Leu Asp Ala Tyr Asn Thr Lys Asp Lys Ile Gly Val Glu Leu Thr
    1970                1975                1980

Gly Arg Thr Leu Ala Asp Leu Thr Leu Leu Asp Ser Pro Ile Lys
    1985                1990                1995

Val Pro Leu Leu Leu Ser Glu Pro Ile Asn Ile Ile Asp Ala Leu
    2000                2005                2010

Glu Met Arg Asp Ala Val Glu Lys Pro Gln Glu Phe Thr Ile Val
    2015                2020                2025

Ala Phe Val Lys Tyr Asp Lys Asn Gln Asp Val His Ser Ile Asn
    2030                2035                2040

Leu Pro Phe Phe Glu Thr Leu Gln Glu Tyr Phe Glu Arg Asn Arg
    2045                2050                2055

Gln Thr Ile Ile Val Val Val Glu Asn Val Gln Arg Asn Leu Lys
    2060                2065                2070

His Ile Asn Ile Asp Gln Phe Val Arg Lys Tyr Arg Ala Ala Leu
    2075                2080                2085

Gly Lys Leu Pro Gln Gln Ala Asn Asp Tyr Leu Asn Ser Phe Asn
    2090                2095                2100

Trp Glu Arg Gln Val Ser His Ala Lys Glu Lys Leu Thr Ala Leu
    2105                2110                2115

Thr Lys Lys Tyr Arg Ile Thr Glu Asn Asp Ile Gln Ile Ala Leu
    2120                2125                2130

Asp Asp Ala Lys Ile Asn Phe Asn Glu Lys Leu Ser Gln Leu Gln
    2135                2140                2145

Thr Tyr Met Ile
    2150

<210> SEQ ID NO 34
<211> LENGTH: 679
<212> TYPE: PRT
<213> ORGANISM: Homo sapiens
<220> FEATURE:
<221> NAME/KEY: MISC_FEATURE
<223> OTHER INFORMATION: Transferrin Region 20-698 of preprotein Acc.
      No. NP_001054.1
```

<400> SEQUENCE: 34

```
Val Pro Asp Lys Thr Val Arg Trp Cys Ala Val Ser Glu His Glu Ala
 1               5                  10                  15
Thr Lys Cys Gln Ser Phe Arg Asp His Met Lys Ser Val Ile Pro Ser
            20                  25                  30
Asp Gly Pro Ser Val Ala Cys Val Lys Lys Ala Ser Tyr Leu Asp Cys
        35                  40                  45
Ile Arg Ala Ile Ala Ala Asn Glu Ala Asp Ala Val Thr Leu Asp Ala
    50                  55                  60
Gly Leu Val Tyr Asp Ala Tyr Leu Ala Pro Asn Asn Leu Lys Pro Val
65                  70                  75                  80
Val Ala Glu Phe Tyr Gly Ser Lys Glu Asp Pro Gln Thr Phe Tyr Tyr
                85                  90                  95
Ala Val Ala Val Val Lys Lys Asp Ser Gly Phe Gln Met Asn Gln Leu
            100                 105                 110
Arg Gly Lys Lys Ser Cys His Thr Gly Leu Gly Arg Ser Ala Gly Trp
        115                 120                 125
Asn Ile Pro Ile Gly Leu Leu Tyr Cys Asp Leu Pro Glu Pro Arg Lys
    130                 135                 140
Pro Leu Glu Lys Ala Val Ala Asn Phe Phe Ser Gly Ser Cys Ala Pro
145                 150                 155                 160
Cys Ala Asp Gly Thr Asp Phe Pro Gln Leu Cys Gln Leu Cys Pro Gly
                165                 170                 175
Cys Gly Cys Ser Thr Leu Asn Gln Tyr Phe Gly Tyr Ser Gly Ala Phe
            180                 185                 190
Lys Cys Leu Lys Asp Gly Ala Gly Asp Val Ala Phe Val Lys His Ser
        195                 200                 205
Thr Ile Phe Glu Asn Leu Ala Asn Lys Ala Asp Arg Asp Gln Tyr Glu
    210                 215                 220
Leu Leu Cys Leu Asp Asn Thr Arg Lys Pro Val Asp Glu Tyr Lys Asp
225                 230                 235                 240
Cys His Leu Ala Gln Val Pro Ser His Thr Val Val Ala Arg Ser Met
                245                 250                 255
Gly Gly Lys Glu Asp Leu Ile Trp Glu Leu Leu Asn Gln Ala Gln Glu
            260                 265                 270
His Phe Gly Lys Asp Lys Ser Lys Glu Phe Gln Leu Phe Ser Ser Pro
        275                 280                 285
His Gly Lys Asp Leu Leu Phe Lys Asp Ser Ala His Gly Phe Leu Lys
    290                 295                 300
Val Pro Pro Arg Met Asp Ala Lys Met Tyr Leu Gly Tyr Glu Tyr Val
305                 310                 315                 320
Thr Ala Ile Arg Asn Leu Arg Glu Gly Thr Cys Pro Glu Ala Pro Thr
                325                 330                 335
Asp Glu Cys Lys Pro Val Lys Trp Cys Ala Leu Ser His His Glu Arg
            340                 345                 350
Leu Lys Cys Asp Glu Trp Ser Val Asn Ser Val Gly Lys Ile Glu Cys
        355                 360                 365
Val Ser Ala Glu Thr Thr Glu Asp Cys Ile Ala Lys Ile Met Asn Gly
    370                 375                 380
Glu Ala Asp Ala Met Ser Leu Asp Gly Gly Phe Val Tyr Ile Ala Gly
385                 390                 395                 400
Lys Cys Gly Leu Val Pro Val Leu Ala Glu Asn Tyr Asn Lys Ser Asp
                405                 410                 415
```

```
Asn Cys Glu Asp Thr Pro Glu Ala Gly Tyr Phe Ala Val Ala Val Val
            420                 425                 430

Lys Lys Ser Ala Ser Asp Leu Thr Trp Asp Asn Leu Lys Gly Lys Lys
            435                 440                 445

Ser Cys His Thr Ala Val Gly Arg Thr Ala Gly Trp Asn Ile Pro Met
            450                 455                 460

Gly Leu Leu Tyr Asn Lys Ile Asn His Cys Arg Phe Asp Glu Phe Phe
465                 470                 475                 480

Ser Glu Gly Cys Ala Pro Gly Ser Lys Lys Asp Ser Ser Leu Cys Lys
            485                 490                 495

Leu Cys Met Gly Ser Gly Leu Asn Leu Cys Glu Pro Asn Asn Lys Glu
            500                 505                 510

Gly Tyr Tyr Gly Tyr Thr Gly Ala Phe Arg Cys Leu Val Glu Lys Gly
            515                 520                 525

Asp Val Ala Phe Val Lys His Gln Thr Val Pro Gln Asn Thr Gly Gly
            530                 535                 540

Lys Asn Pro Asp Pro Trp Ala Lys Asn Leu Asn Glu Lys Asp Tyr Glu
545                 550                 555                 560

Leu Leu Cys Leu Asp Gly Thr Arg Lys Pro Val Glu Glu Tyr Ala Asn
            565                 570                 575

Cys His Leu Ala Arg Ala Pro Asn His Ala Val Val Thr Arg Lys Asp
            580                 585                 590

Lys Glu Ala Cys Val His Lys Ile Leu Arg Gln Gln Gln His Leu Phe
            595                 600                 605

Gly Ser Asn Val Thr Asp Cys Ser Gly Asn Phe Cys Leu Phe Arg Ser
            610                 615                 620

Glu Thr Lys Asp Leu Leu Phe Arg Asp Asp Thr Val Cys Leu Ala Lys
625                 630                 635                 640

Leu His Asp Arg Asn Thr Tyr Glu Lys Tyr Leu Gly Glu Glu Tyr Val
            645                 650                 655

Lys Ala Val Gly Asn Leu Arg Lys Cys Ser Thr Ser Ser Leu Leu Glu
            660                 665                 670

Ala Cys Thr Phe Arg Arg Pro
            675

<210> SEQ ID NO 35
<211> LENGTH: 544
<212> TYPE: PRT
<213> ORGANISM: Homo sapiens
<220> FEATURE:
<221> NAME/KEY: MISC_FEATURE
<223> OTHER INFORMATION: IhHG1 Acc. No. AAH19046

<400> SEQUENCE: 35

Met Glu Phe Gly Leu Ser Trp Val Phe Leu Val Ala Leu Leu Arg Gly
1               5                   10                  15

Val Gln Cys Gln Ala Gln Leu Val Glu Ser Gly Gly Gly Val Val Gln
            20                  25                  30

Pro Gly Ser Ser Leu Arg Leu Ser Cys Ala Ala Ser Gly Phe Arg Phe
            35                  40                  45

Ser Asn Tyr Gly Met His Trp Val Arg Gln Ala Pro Gly Lys Gly Leu
            50                  55                  60

Glu Trp Val Ala Val Phe Ser Tyr Asp Glu Ser Asp Lys Tyr Tyr Ala
65                  70                  75                  80

Ala Ser Val Lys Gly Arg Phe Thr Ile Ser Arg Asp Asn Ser Lys Asn
            85                  90                  95
```

```
Thr Leu Ser Leu Gln Met Asn Ser Leu Arg Val Glu Asp Thr Ala Val
            100                 105                 110
Tyr Tyr Cys Ala Lys Asp Gln Lys Pro Trp Tyr Ser Asn Ser Trp Phe
        115                 120                 125
Leu Thr Asn Phe Asp Ser Trp Gly Arg Gly Thr Leu Val Thr Val Ser
    130                 135                 140
Ser Ala Ser Thr Lys Gly Pro Ser Val Phe Pro Leu Ala Pro Ser Ser
145                 150                 155                 160
Lys Ser Thr Ser Gly Gly Thr Ala Ala Leu Gly Cys Leu Val Lys Asp
                165                 170                 175
Tyr Phe Pro Glu Pro Val Thr Val Ser Trp Asn Ser Gly Ala Leu Thr
            180                 185                 190
Ser Gly Val His Thr Phe Pro Ala Val Leu Gln Ser Ser Gly Leu Tyr
        195                 200                 205
Ser Leu Ser Ser Val Val Thr Val Pro Ser Ser Ser Leu Gly Thr Gln
    210                 215                 220
Thr Tyr Ile Cys Asn Val Asn His Lys Pro Ser Asn Thr Lys Val Asp
225                 230                 235                 240
Lys Lys Val Glu Pro Lys Ser Cys Asp Lys Thr His Thr Cys Pro Pro
                245                 250                 255
Cys Pro Ala Pro Glu Leu Leu Gly Gly Pro Ser Val Phe Leu Phe Pro
            260                 265                 270
Pro Lys Pro Lys Asp Thr Leu Met Ile Ser Arg Thr Pro Glu Val Thr
        275                 280                 285
Cys Val Val Val Asp Val Ser His Glu Asp Pro Glu Val Lys Phe Asn
    290                 295                 300
Trp Tyr Val Asp Gly Val Glu Val His Asn Ala Lys Thr Lys Pro Arg
305                 310                 315                 320
Glu Glu Gln Tyr Asn Ser Thr Tyr Arg Val Val Ser Val Leu Thr Val
                325                 330                 335
Leu His Gln Asp Trp Leu Asn Gly Lys Glu Tyr Lys Cys Lys Val Ser
            340                 345                 350
Asn Lys Ala Leu Pro Ala Pro Ile Glu Lys Thr Ile Ser Lys Ala Lys
        355                 360                 365
Gly Gln Pro Arg Glu Pro Gln Val Tyr Thr Leu Pro Pro Ser Arg Asp
    370                 375                 380
Glu Leu Thr Lys Asn Gln Val Ser Leu Thr Cys Leu Val Lys Gly Phe
385                 390                 395                 400
Tyr Pro Ser Asp Ile Ala Val Glu Trp Glu Ser Asn Gly Gln Pro Glu
                405                 410                 415
Asn Asn Tyr Lys Thr Thr Pro Pro Val Leu Asp Ser Asp Gly Ser Phe
            420                 425                 430
Phe Leu Tyr Ser Lys Leu Thr Val Asp Lys Ser Arg Trp Gln Gln Gly
        435                 440                 445
Asn Val Phe Ser Cys Ser Val Met His Glu Ala Leu His Asn His Tyr
    450                 455                 460
Thr Gln Lys Ser Leu Ser Leu Ser Pro Glu Leu Gln Leu Glu Glu Ser
465                 470                 475                 480
Cys Ala Glu Ala Gln Asp Gly Glu Leu Asp Gly Leu Trp Thr Thr Ile
                485                 490                 495
Thr Ile Phe Ile Thr Leu Phe Leu Leu Ser Val Cys Tyr Ser Ala Thr
            500                 505                 510
Val Thr Phe Phe Lys Val Lys Trp Ile Phe Ser Ser Val Val Asp Leu
```

```
                515                 520                 525
Lys Gln Thr Ile Ile Pro Asp Tyr Arg Asn Met Ile Gly Gln Gly Ala
    530                 535                 540
```

<210> SEQ ID NO 36
<211> LENGTH: 406
<212> TYPE: PRT
<213> ORGANISM: Homo sapiens
<220> FEATURE:
<221> NAME/KEY: MISC_FEATURE
<223> OTHER INFORMATION: Haptoglobin Acc. No. NP_005134.1

<400> SEQUENCE: 36

```
Met Ser Ala Leu Gly Ala Val Ile Ala Leu Leu Leu Trp Gly Gln Leu
1               5                   10                  15

Phe Ala Val Asp Ser Gly Asn Asp Val Thr Asp Ile Ala Asp Asp Gly
                20                  25                  30

Cys Pro Lys Pro Pro Glu Ile Ala His Gly Tyr Val Glu His Ser Val
            35                  40                  45

Arg Tyr Gln Cys Lys Asn Tyr Tyr Lys Leu Arg Thr Glu Gly Asp Gly
        50                  55                  60

Val Tyr Thr Leu Asn Asp Lys Lys Gln Trp Ile Asn Lys Ala Val Gly
65                  70                  75                  80

Asp Lys Leu Pro Glu Cys Glu Ala Asp Asp Gly Cys Pro Lys Pro Pro
                85                  90                  95

Glu Ile Ala His Gly Tyr Val Glu His Ser Val Arg Tyr Gln Cys Lys
            100                 105                 110

Asn Tyr Tyr Lys Leu Arg Thr Glu Gly Asp Gly Val Tyr Thr Leu Asn
        115                 120                 125

Asn Glu Lys Gln Trp Ile Asn Lys Ala Val Gly Asp Lys Leu Pro Glu
    130                 135                 140

Cys Glu Ala Val Cys Gly Lys Pro Lys Asn Pro Ala Asn Pro Val Gln
145                 150                 155                 160

Arg Ile Leu Gly Gly His Leu Asp Ala Lys Gly Ser Phe Pro Trp Gln
                165                 170                 175

Ala Lys Met Val Ser His His Asn Leu Thr Thr Gly Ala Thr Leu Ile
            180                 185                 190

Asn Glu Gln Trp Leu Leu Thr Thr Ala Lys Asn Leu Phe Leu Asn His
        195                 200                 205

Ser Glu Asn Ala Thr Ala Lys Asp Ile Ala Pro Thr Leu Thr Leu Tyr
    210                 215                 220

Val Gly Lys Lys Gln Leu Val Glu Ile Glu Lys Val Val Leu His Pro
225                 230                 235                 240

Asn Tyr Ser Gln Val Asp Ile Gly Leu Ile Lys Leu Lys Gln Lys Val
                245                 250                 255

Ser Val Asn Glu Arg Val Met Pro Ile Cys Leu Pro Ser Lys Asp Tyr
            260                 265                 270

Ala Glu Val Gly Arg Val Gly Tyr Val Ser Gly Trp Gly Arg Asn Ala
        275                 280                 285

Asn Phe Lys Phe Thr Asp His Leu Lys Tyr Val Met Leu Pro Val Ala
    290                 295                 300

Asp Gln Asp Gln Cys Ile Arg His Tyr Glu Gly Ser Thr Val Pro Glu
305                 310                 315                 320

Lys Lys Thr Pro Lys Ser Pro Val Gly Val Gln Pro Ile Leu Asn Glu
                325                 330                 335

His Thr Phe Cys Ala Gly Met Ser Lys Tyr Gln Glu Asp Thr Cys Tyr
```

```
                340                 345                 350
Gly Asp Ala Gly Ser Ala Phe Ala Val His Asp Leu Glu Glu Asp Thr
            355                 360                 365
Trp Tyr Ala Thr Gly Ile Leu Ser Phe Asp Lys Ser Cys Ala Val Ala
        370                 375                 380
Glu Tyr Gly Val Tyr Val Lys Val Thr Ser Ile Gln Asp Trp Val Gln
385                 390                 395                 400
Lys Thr Ile Ala Glu Asn
                405

<210> SEQ ID NO 37
<211> LENGTH: 9
<212> TYPE: PRT
<213> ORGANISM: Homo sapiens

<400> SEQUENCE: 37

Glu Lys Leu His Glu Leu Gln Glu Lys
1               5

<210> SEQ ID NO 38
<211> LENGTH: 9
<212> TYPE: PRT
<213> ORGANISM: Homo sapiens

<400> SEQUENCE: 38

Gln Lys Leu His Glu Leu Gln Glu Lys
1               5

<210> SEQ ID NO 39
<211> LENGTH: 9
<212> TYPE: PRT
<213> ORGANISM: Homo sapiens

<400> SEQUENCE: 39

Glu Lys Leu His Glu Leu Gln Glu Lys
1               5

<210> SEQ ID NO 40
<211> LENGTH: 9
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa is pyroglutamate

<400> SEQUENCE: 40

Gln Lys Leu His Xaa Leu Gln Glu Lys
1               5

<210> SEQ ID NO 41
<211> LENGTH: 9
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa is pyroglutamate

<400> SEQUENCE: 41

Glu Lys Leu His Xaa Leu Gln Glu Lys
1               5

<210> SEQ ID NO 42
<211> LENGTH: 9
```

```
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa is pyroglutamate

<400> SEQUENCE: 42

Gln Lys Leu His Xaa Leu Glu Glu Lys
1               5

<210> SEQ ID NO 43
<211> LENGTH: 9
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa is pyroglutamate

<400> SEQUENCE: 43

Glu Lys Leu His Xaa Leu Glu Glu Lys
1               5

<210> SEQ ID NO 44
<211> LENGTH: 11
<212> TYPE: PRT
<213> ORGANISM: Homo sapiens

<400> SEQUENCE: 44

Leu Glu Ala Leu Lys Glu Asp Gly Gly Ala Arg
1               5                   10

<210> SEQ ID NO 45
<211> LENGTH: 11
<212> TYPE: PRT
<213> ORGANISM: Homo sapiens

<400> SEQUENCE: 45

Val Glu Pro Tyr Leu Asp Asp Phe Gln Lys Lys
1               5                   10

<210> SEQ ID NO 46
<211> LENGTH: 11
<212> TYPE: PRT
<213> ORGANISM: Homo sapiens

<400> SEQUENCE: 46

Val Gln Pro Tyr Leu Asp Asp Phe Glu Lys Lys
1               5                   10

<210> SEQ ID NO 47
<211> LENGTH: 11
<212> TYPE: PRT
<213> ORGANISM: Homo sapiens

<400> SEQUENCE: 47

Val Glu Pro Tyr Leu Asp Asp Phe Glu Lys Lys
1               5                   10
```